(12) United States Patent
Freeman et al.

(10) Patent No.: US 10,799,149 B2
(45) Date of Patent: Oct. 13, 2020

(54) ANALYSIS OF SKIN COLORATION

(71) Applicant: ZOLL Medical Corporation, Chelmsford, MA (US)

(72) Inventors: Gary A. Freeman, Newton Center, MA (US); Ulrich Herken, Medford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 1098 days.

(21) Appl. No.: 14/295,688

(22) Filed: Jun. 4, 2014

(65) Prior Publication Data

US 2014/0378779 A1 Dec. 25, 2014

Related U.S. Application Data

(60) Provisional application No. 61/836,803, filed on Jun. 19, 2013.

(51) Int. Cl.
*A61B 5/103* (2006.01)
*A61B 5/02* (2006.01)
(Continued)

(52) U.S. Cl.
CPC .......... *A61B 5/1032* (2013.01); *A61B 5/0048* (2013.01); *A61B 5/0051* (2013.01); *A61B 5/0053* (2013.01); *A61B 5/0064* (2013.01); *A61B 5/0077* (2013.01); *A61B 5/0205* (2013.01); *A61B 5/02042* (2013.01); *A61B 5/02055* (2013.01); *A61B 5/14551* (2013.01); *A61B 5/483* (2013.01); *A61B 5/7246* (2013.01); *A61B 5/7282* (2013.01); *A61B 5/742* (2013.01); *A61B 5/746* (2013.01); *A61B 5/0075* (2013.01); *A61B 5/021* (2013.01); *A61B 5/0836* (2013.01); *A61B 5/6805* (2013.01); *A61B 5/6898* (2013.01);
(Continued)

(58) Field of Classification Search
CPC ....... A61B 5/441; A61B 5/443; A61B 5/1032; A61B 5/02055; A61B 5/7282; A61B 5/7275
See application file for complete search history.

(56) References Cited

U.S. PATENT DOCUMENTS 4,723,554 A 2/1988 Oman et al.
4,724,844 A * 2/1988 Rafelson ............. A61B 5/0205
312/111
(Continued)

FOREIGN PATENT DOCUMENTS

WO WO 01/50970 7/2001
WO WO 01/54581 8/2001
WO WO-2012/117316 A2 * 9/2012 ............... A61B 5/00

OTHER PUBLICATIONS

"Precise Color Communication: Color Control from Perception to Instrumentation." Konica Minolta. 2007. 62 pages. (Year: 2007).*
(Continued)

*Primary Examiner* — Meredith Weare
(74) *Attorney, Agent, or Firm* — Finch & Maloney PLLC

(57) ABSTRACT

This document relates to computer-based systems and techniques for analyzing skin coloration using spectral imaging techniques to determine a medical condition of an individual. This document further relates to providing feedback to a rescuer or other medical professional based on the colorimetric properties of the patient's skin.

55 Claims, 12 Drawing Sheets

(51) Int. Cl.
*A61B 5/00* (2006.01)
*A61B 5/0205* (2006.01)
*A61B 5/1455* (2006.01)
*A61N 1/39* (2006.01)
*A61B 5/021* (2006.01)
*A61B 5/083* (2006.01)
*A61N 1/36* (2006.01)

(52) U.S. Cl.
CPC ......... *A61B 5/7275* (2013.01); *A61B 2505/01* (2013.01); *A61B 2576/02* (2013.01); *A61N 1/36014* (2013.01); *A61N 1/3925* (2013.01)

(56) References Cited

U.S. PATENT DOCUMENTS

| | | | | |
|---|---|---|---|---|
| 5,272,518 | A * | 12/1993 | Vincent | G01J 3/12 250/226 |
| 5,963,333 | A | 10/1999 | Walowit et al. | |
| 6,157,445 | A * | 12/2000 | Macfarlane | A61B 5/0088 356/243.5 |
| 6,271,920 | B1 * | 8/2001 | Macfarlane | G01J 3/52 356/243.5 |
| 7,620,212 | B1 | 11/2009 | Allen et al. | |
| 8,116,838 | B2 | 2/2012 | Gaspard et al. | |
| 2003/0212316 | A1 | 11/2003 | Leiden et al. | |
| 2004/0078299 | A1 | 4/2004 | Down-Logan et al. | |
| 2004/0249290 | A1 * | 12/2004 | Shani | A61B 5/0059 600/476 |
| 2006/0234383 | A1 * | 10/2006 | Gough | A61B 5/0059 436/63 |
| 2006/0246020 | A1 | 11/2006 | Cole et al. | |
| 2009/0143694 | A1 * | 6/2009 | Krauss | A61B 5/0205 600/532 |
| 2009/0171237 | A1 * | 7/2009 | Campbell | A61B 5/053 600/547 |
| 2009/0299154 | A1 * | 12/2009 | Segman | A61B 5/0059 600/301 |
| 2009/0306484 | A1 * | 12/2009 | Kurtz | A61B 5/442 600/300 |
| 2010/0092441 | A1 * | 4/2010 | Lundberg | A61K 31/05 424/93.45 |
| 2010/0100392 | A1 * | 4/2010 | Rothman | G06Q 50/22 705/2 |
| 2010/0241016 | A1 * | 9/2010 | Bowman | A61B 5/028 600/504 |
| 2010/0280333 | A1 * | 11/2010 | Parshuram | G06F 19/3418 600/301 |
| 2012/0130211 | A1 | 5/2012 | Kobayashi et al. | |
| 2012/0220845 | A1 * | 8/2012 | Campbell | A61B 5/0836 600/364 |
| 2012/0289809 | A1 * | 11/2012 | Kaib | A61B 5/04085 600/388 |
| 2013/0245400 | A1 * | 9/2013 | Kuo | A61B 5/1032 600/306 |
| 2013/0338543 | A1 * | 12/2013 | Gegner | A61B 5/0002 600/595 |
| 2014/0078301 | A1 * | 3/2014 | Fazzi | A61B 5/0059 348/143 |

OTHER PUBLICATIONS

International Search Report and Written Opinion, PCT/US2014/040869, dated Nov. 3, 2014, 22 pages.
Angelopoulou, Elli, "The Reflectance Spectrum of Human Skin," Technical Reports (CIS), University of Pennsylvania Department of Computer & Information Science, Dec. 20, 1999, 15 pages.
Angelopoulou, Elli, "Understanding the color of human skin," SPIE Conference on Human Vision and Electronic Imaging VI, 2001, SPIE 4299, 243-251.
Bersha, Kusse Sukuta, "Spectral Imaging and Analysis of Human Skin," Master Thesis Report, University of Eastern Finland, Jun. 21, 2010, 66 pages.
"CIE 1931 color space," Wikipedia, accessed online http://en.wikipedia.org/wiki/CIE_XYZ_color_space Jun. 12, 2013, 12 pages.
"Color Data Software CM-S100w SpectraMagic™NX," Konica Minolta Sensing, Inc., 2007, 6 pages.
Doi, Motonori, et al., "Spectral Reflectance Estimation of Human Skin and Its Application to Image Rendering," Journal of Imaging Science and Technology, vol. 49, No. 6, Nov./Dec. 2005, 29 pages.
"Jaundice Meter JM-103," Konica Minolta Sensing, Inc., 2002, 2 pages.
"Lab color space," Wikipedia, accessed online < http://en.wikipedia.org/wiki/CIELAB> Jun. 12, 2013, 8 pages.
"Lightness," Wikipedia, accessed online http://en.wikipedia.org/wiki/Lightness_%28color%29 Jun. 12, 2013, 5 pages.
"Nicotinamide adenine dinucleotide," Wikipedia, accessed online http://en.wikipedia.org/wiki/Nicotinamide_adenine_dinucleotide Jun. 12, 2013, 12 pages.
"Opponent process," Wikipedia, accessed online http://en.wikipedia.org/wiki/Opponent_process Jun. 12, 2013, 5 pages.
Osorio, Daniel et al., "Measuring Skin Colour and Spectral Reflectance Using a Digital Camera," University of Sussex, 2007, 5 pages.
Park Jung-Hun, et al., "A Study of Skin Color by Melanin Index According to Site, Gestational Age, Birth Weight and Season of Birth in Korean Neonates," J. Korean Med. Sci. 2005, 20:105-108.
"Precise Color Communication," Konica Minolta Sensing, Inc., 2003, accessed online http://www2.konicaminolta.eu/eu/Measuring/pcc/en/index.html 1 page.
"Skin Analysis Software CM-SA," Konica Minolta Sensing Americas, Inc., downloaded on Jun. 14, 2013, http://sensing.konicaminolta.com.br/wp-content/uploads/2011/05/CMSA_software_usa.pdf, 4 pages.
"Spectrophotometer CM-700d/600d," Konica Minolta Sensing, Inc., 2007, 2 pages.
"Spectrophotometer CM-700d/600d Instruction Manual," Konica Minolta Sensing, Inc., downloaded on Jun. 14, 2013, http://sensing.konicaminolta.us/wp-content/uploads/2011/05/CM-700d_600dEA.pdf, 124 pages.
Wagner, Jennifer K., et al., "Comparing Quantitative Measures of Erythema, Pigmentation and Skin Response using Reflectometry," Pigment Cell Res, 15: 379-384, Jul. 22, 2002.

* cited by examiner

ANALYSIS OF SKIN COLORATION

CLAIM OF PRIORITY

This application claims priority under 35 U.S.C. § 119(e) to U.S. Provisional Application Ser. No. 61/836,803, filed on Jun. 19, 2013, the entire contents of which are hereby incorporated by reference.

TECHNICAL FIELD

This document relates to computer-based systems and techniques for analyzing skin coloration using spectral imaging techniques to determine a medical condition of an individual. This document further relates to providing feedback to a rescuer or other medical professional based on the colorimetric properties of the patient's skin.

BACKGROUND

Various mechanisms are used by EMTs, rescuers, and medical professionals to evaluate the degree of illness of a victim or patient. One such mechanism is the modified early warning score (MEWS). MEWS is based on data derived from four physiological readings (systolic blood pressure, heart rate, respiratory rate, and body temperature) and one observation such as level of consciousness or a score based on the alert, voice, pain, unresponsive (AVPU) scale. The resulting observations are compared to a normal range to generate a single composite score. In addition, often medical professionals have a sense or intuition about when a patient will crash and code. For example, an experienced nurse or medical professional may be able to assess a patient's condition based on coloration of the patient.

SUMMARY

During treatment of a patient or victim preventing delay in intervention or treatment as conditions change can greatly increase the success of the treatment. However, it can be difficult to identify patients who are in danger of deterioration. Skin color (e.g., based on spectral reflectance) can provide an important indicator of physiological state. Systems and methods described herein collect, monitor, and analyze reflectance/absorption data to determine changes in a patient's condition. The information gathered from the spectral reflectance or absorption data can be used to signal when a patient is experiencing decreased blood circulation (e.g., is about to crash), decreased liver function, and/or other conditions for which a medical professional should likely intervene.

In certain aspects, a computer-implemented method includes obtaining color information based on an intensity of light reflected primarily from the epidermis and dermal papillae of an individual's skin, analyzing the color information to determine the colorimetric properties of the individual's skin, generating, from the analysis of the colorimetric properties of the skin, a metric that provides data indicative of a medical status of the individual, and providing, for display to a user, a visual summary including the metric.

Embodiments can include one or more of the following.

The colorimetric properties can include coordinates in a color space.

The color space can be a color space selected from the group consisting of a Lab color space, a L*a*b* color space, and a XYZ color space.

The color space can be a color space having higher dimensionality than three and having associated stimulus functions.

The color space can be a quadrastimulus color space.

The color space can be a pentastimulus color space.

The stimulus functions can include stimulus functions configured to enhance detection of an underlying physiologic state.

The underlying physiologic state can include detection of NAD and NADH.

Obtaining the color information can include obtaining the color information from a device included in a wearable device comprising a lifevest or holter-like monitoring product.

The method can also include sensing one or more parameters including one or more of blood pressure, end tidal carbon dioxide (EtC02), and blood oxygen saturation (Sp02), wherein generating the metric comprises generating the metric based on the analyzed colorimetric properties and the one or more sensed parameters.

The method can also include obtaining baseline colorimetric properties based on an intensity of light radiation reflected from the individual's skin.

Analyzing the colorimetric properties can include comparing the obtained colorimetric properties with the obtained baseline colorimetric properties to determine an amount of change between the obtained colorimetric properties and the baseline colorimetric properties, comparing the amount of change between the obtained colorimetric properties and the baseline colorimetric properties to a threshold, and alerting the user when the amount of change exceeds the threshold.

The method can also include updating the baseline colorimetric properties upon determining that the change between the obtained colorimetric properties and the baseline colorimetric properties exceeds the threshold.

The method can also include calculating a risk score that provides a measure of the risk of an impending acute medical event (IAME).

The method can also include calculating a risk score that provides a measure of the risk of one or more of a cardiac arrest, syncopal episode, traumatic arrest due to such causes as internal bleeding, blunt force trauma, various causes of hypovolemia and heart attack.

The method can also include providing a warning based on the risk score exceeding an established threshold.

Obtaining the color information can include obtaining baseline colorimetric properties based on an intensity of light radiation reflected from the individual's skin, applying a stimulus configured to produce a change in the colorimetric properties of the individual's skin, and obtaining one or more additional measurements of the colorimetric properties at times selected to capture changes in the colorimetric properties of the individual's skin based on the applied stimulus.

Analyzing the colorimetric properties can include comparing the obtained colorimetric properties with the obtained baseline colorimetric properties to determine an amount of change between the obtained colorimetric properties and the baseline colorimetric properties in response to the applied stimulus.

Applying the stimulus can include applying a pressure to the individual's skin.

Applying the pressure to the individual's skin can include applying the pressure using an air filled bladder that presses against the skin then releases.

Applying the stimulus can include providing an audio stimulus.

Applying the stimulus can include stimulating skin with electricity.

Applying the stimulus can include applying a stimulus configured to generate a pain sensation.

Applying the stimulus can include providing audio signal or voice generated signal configured to elicit a response.

Obtaining the colorimetric properties can include obtaining the colorimetric properties via a camera in a portable telephone.

The color information can be a spectra.

The spectra can be an absorption spectra for wavelengths between 500 and 600 nm.

The spectra can be a reflectance spectra for wavelengths between 500 and 600 nm.

The color information can be luminance information for each of multiple colors.

The color information can be luminance information for red, green and blue components collected by a charge-coupled device (CCD).

In some aspects, a system for determining information about a patient status based on colorimetric properties of the individual's skin includes a colorimeter configured to obtain a color information based on an intensity of light reflected primarily from the epidermis and dermal papillae of an individual's skin, a processor configured to analyze the color information to determine the colorimetric properties of the individual's skin and generate, from the analysis of the colorimetric properties of the skin, a metric that provides data indicative of a medical status of the individual, and a display device configured to display a visual summary including the metric.

Embodiments can include one or more of the following.

The colorimetric properties can include coordinates in a color space.

The color space can be a color space selected from the group consisting of a Lab color space, a L*a*b* color space, and a XYZ color space.

The color space can be a color space having higher dimensionality than three and having associated stimulus functions.

The color space can be a quadrastimulus color space.

The color space can be a pentastimulus color space.

The stimulus functions can include stimulus functions configured to enhance detection of an underlying physiologic state.

The underlying physiologic state can be detection of NAD and NADH.

The colorimeter can be disposed within in a wearable device like lifevest or holter-like monitoring product The system can also include one or more sensors configured to measure one or more parameters including one or more of blood pressure, end tidal carbon dioxide (EtC02), and blood oxygen saturation (Sp02), wherein the processor is further configured to generate the metric based on the analyzed colorimetric properties and the one or more sensed parameters.

The processor can be further configured to cause the colorimeter to obtain a baseline colorimetric properties based on an intensity of light radiation reflected from the individual's skin.

The processor can be further configured to analyze the colorimetric properties by comparing the obtained colorimetric properties with the obtained baseline colorimetric properties to determine an amount of change between the obtained colorimetric properties and the baseline colorimetric properties, comparing the amount of change between the obtained colorimetric properties and the baseline colorimetric properties to a threshold, and alerting the user when the amount of change exceeds the threshold.

The processor can be further configured to update the baseline colorimetric properties upon determining that the change between the obtained colorimetric properties and the baseline colorimetric properties exceeds the threshold.

The processor can be further configured to calculate a risk score that provides a measure of the risk of an impending acute medical event (IAME).

The processor can be further configured to calculate a risk score that provides a measure of the risk of one or more of a cardiac arrest, syncopal episode, traumatic arrest due to such causes as internal bleeding, blunt force trauma, various causes of hypovolemia and heart attack.

The processor can be further configured to provide a warning based on the risk score exceeding an established threshold.

The processor can be further configured to obtain the color information by obtaining baseline colorimetric properties based on an intensity of light radiation reflected from the individual's skin, applying a stimulus configured to produce a change in the colorimetric properties of the individual's skin, and obtaining one or more additional measurements of the colorimetric properties at times selected to capture changes in the colorimetric properties of the individual's skin based on the applied stimulus.

The processor can be further configured to analyze the colorimetric properties by comparing the obtained colorimetric properties with the obtained baseline colorimetric properties to determine an amount of change between the obtained colorimetric properties and the baseline colorimetric properties in response to the applied stimulus.

The colorimeter can be a camera in a portable telephone.

The color information can include an absorption spectra for wavelengths between 500 and 600 nm.

The color information can include a reflectance spectra for wavelengths between 500 and 600 nm.

The details of one or more embodiments are set forth in the accompanying drawings and the description below. Other features and advantages will be apparent from the description and drawings, and from the claims.

DETAILED DESCRIPTION

This description discusses examples of implementations that may be employed in capturing and analyzing color information such as spectral reflectance or absorption data from a patient or victim and generating colorimetric data and other color-descriptive metrics, trending data, and/or alerts based on the analyzed spectral reflectance or absorption data. The spectral reflectance or absorption data provides an indicator of skin color, which can be an important indicator of physiological status.

Figure 1:
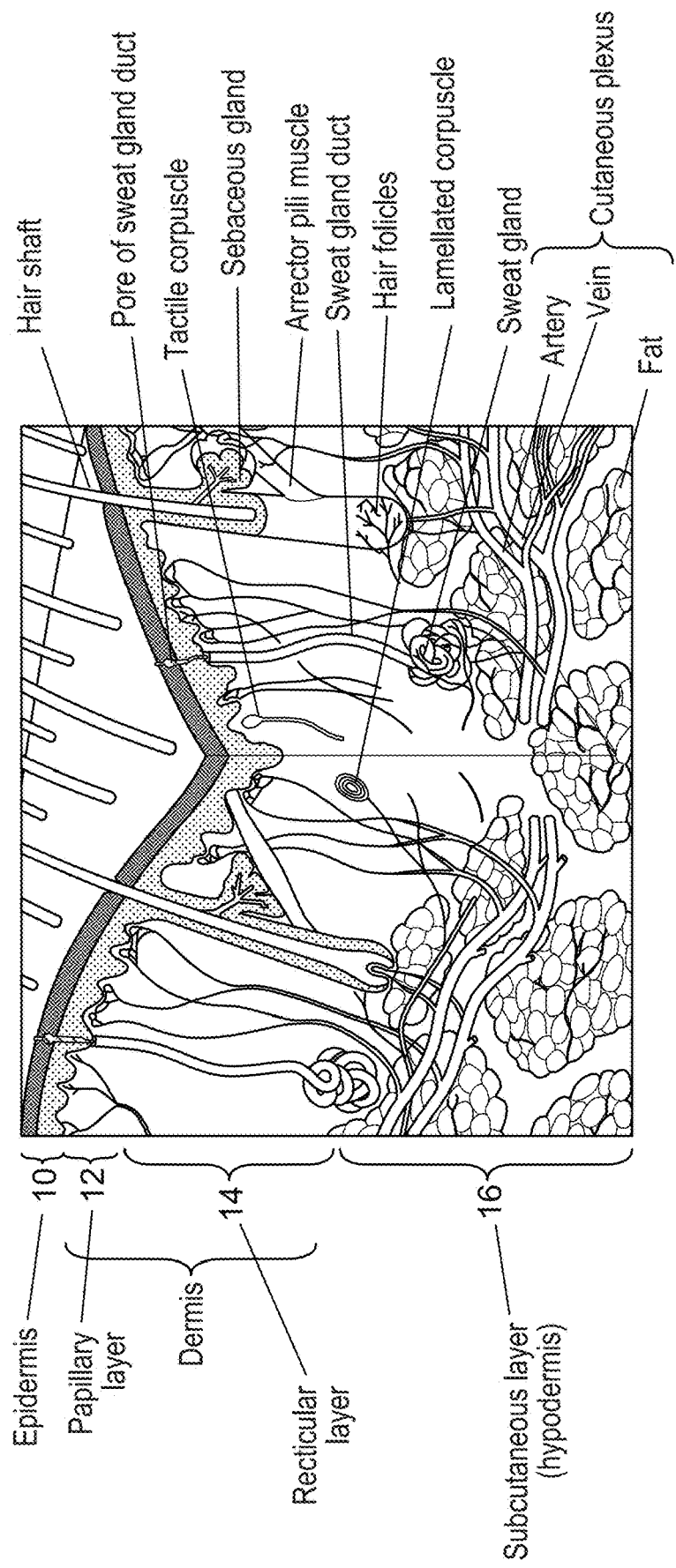
FIG. 1 shows an exemplary diagram of the skin.

Skin color or skin pallor differs from other known non-invasive, spectrographic analyses of tissue such as pulse oximetry (e.g., pulse oximetry systems such as those available from Masimo) or near-infrared spectroscopy (e.g., near-infrared spectroscopy systems such as those available from Reflectance Technology, Westford, Mass.) in that skin color or pallor primarily analyzes the reflected spectrum from the very outermost layers of the skin in the stratum corneum, epidermis layer 10 and papillary layer 12, as opposed to oximetry or other known spectrographic tissue analysis which analyzes either the light reflected, transmitted or scattered from the reticular dermal 14, subcutaneous 16 or skeletal muscle layers of the body as shown in FIG. 1.

Figure 2:
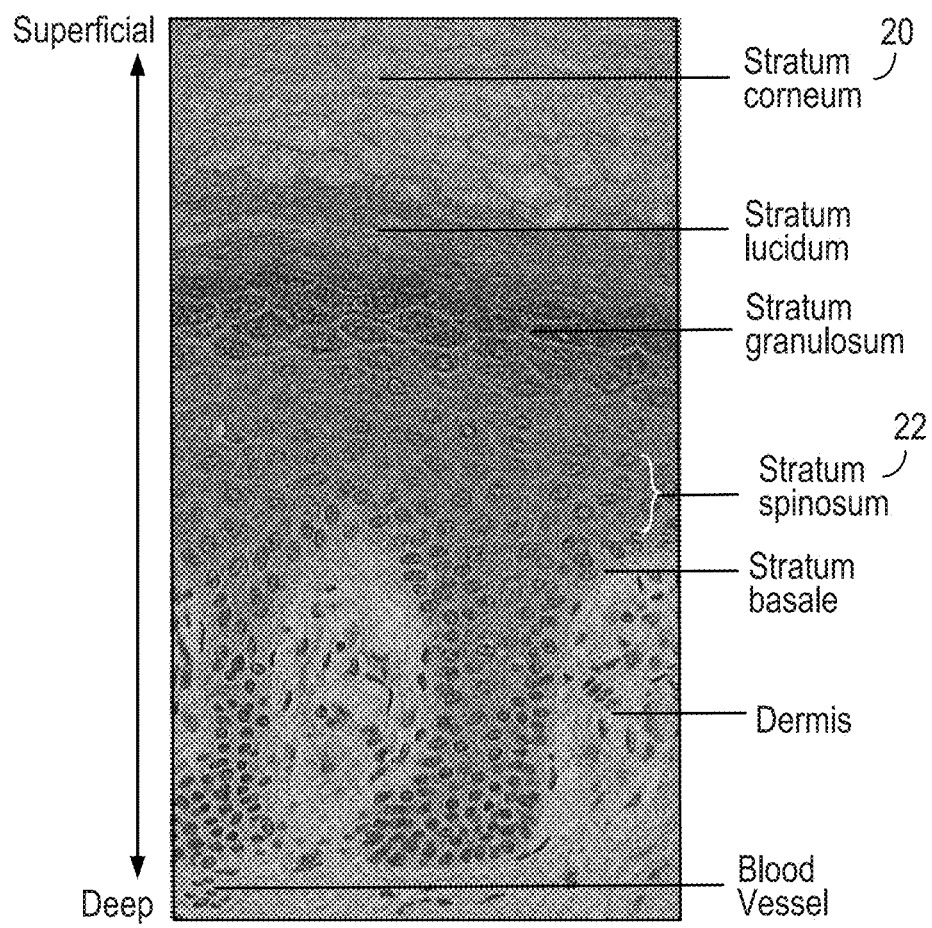
FIG. 2 shows an exemplary diagram of various components of the skin.

Referring now to FIG. 2, skin color is composed of three primary components:

Structural elements—A static color resulting from the stratum corneum layer 20 composed of dead skin cells and other material, as well as hair, arrector pili muscles for hairs that connect in the papillae as well as the cell materials themselves of the skin cells.

Pigmentation—A very slowly changing color (on the order of 24 hours, such as with tanning) resulting primarily from skin pigmentation due to various forms of melanin: Phoemelanin which gives a yellow-red color to skin, Eumelanin—gives a black-brown color to skin, and also by carotene which interacts with eumelanin in Asian populations. Pigmentation is generally localized in the stratum spinosum 22 and is due to melanocytes and melanosomes.

Figure 3:
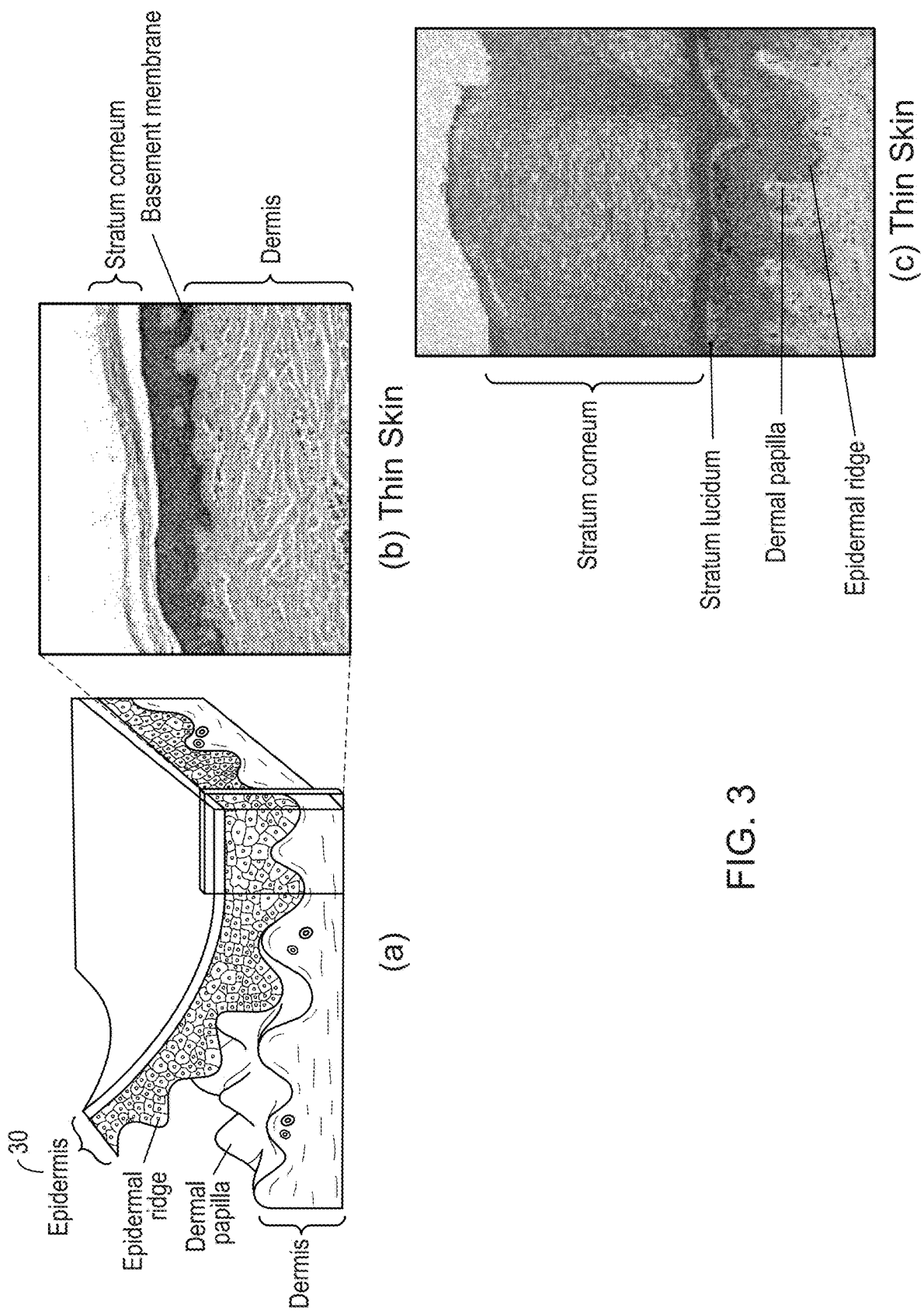
FIG. 3a-c shows an exemplary diagram of the epidermis and dermis.

Pallor—A more rapidly changing cause (on the order of seconds, minutes or hours), pallor may be due to physiologic-related conditions like jaundice, which cause a build-up and subsequent diffusion into the epidermis of spectral-modifying chemicals like bilirubin (in the case of bilirubin, a yellowish hue). Pallor may also be due to the effect of oxygen and other metabolites on the spectrum of the capillaries in the dermal papillae that invaginate the inner surface of the epidermis 30 (FIG. 3).

Optical absorption in blood is due primarily to hemoglobin which includes both oxyhemoglobin 226 and deoxyhemoglobin 224 (FIG. 9), which have slightly different absorption spectra. Deoxyhemoglobin has absorption maxima at around 430 nm, 555 nm, and 760 nm, while oxyhemoglobin has an absorption minima around 680 nm. Hemoglobin is found in the capillary microvascular network of the dermis, typically 50±500 µm below the skin surface, e.g., in layer 222. This wavelength dependence of the absorption is the reason for the red color of blood. Another class of compounds that accounts for much of the absorption in the skin is melanin 220. Since human skin is characterized by variable concentration in melanin 220, analysis of spectral absorption or reflectance data in order to determine a patient's medical condition includes factoring out the contribution of melanin 220 to the absorption. In one example, this can be done by analyzing particular ranges of wavelengths and/or by analyzing changes or shifts in the measured spectral absorption or reflectance data.

This invention uses skin pallor, as opposed to conventional vascular spectrum like pulse oximetry, as a diagnostic for patient health and progression of patient health.

In treatment of the patient or victim, pallor is an important factor in medical diagnosis and in determining whether the patient's condition is improving or deteriorating. The capillaries contained in the dermal papillae are the most sensitive to changes in the patient's status, as they are the smallest vessels and the first to vasoconstrict or dilate with any alteration of the patient's underlying physiologic status. Diagnostic measures employing spectrographic analysis of light from the capillaries contained in the dermal papillae will thus provide clinicians with an earlier warning than existing methods of a patient's impending degradation in physiologic status. For example, when oxygen saturation in the blood decreases, a shift in color from red to blue will be observed, or when liver function is decreasing due to jaundice, a shift in color toward yellow will be observed. When the capillaries contained in the dermal papillae constrict, the skin pallor will grow progressively more pale. Thus, quantitative colorimetric information about how the spectral and colorimetric properties of the patient's skin change over time can be used as predictors of patient status and/or condition. In some examples, this quantitative information can be used as a predictor for cardiac arrest.

Figure 4:
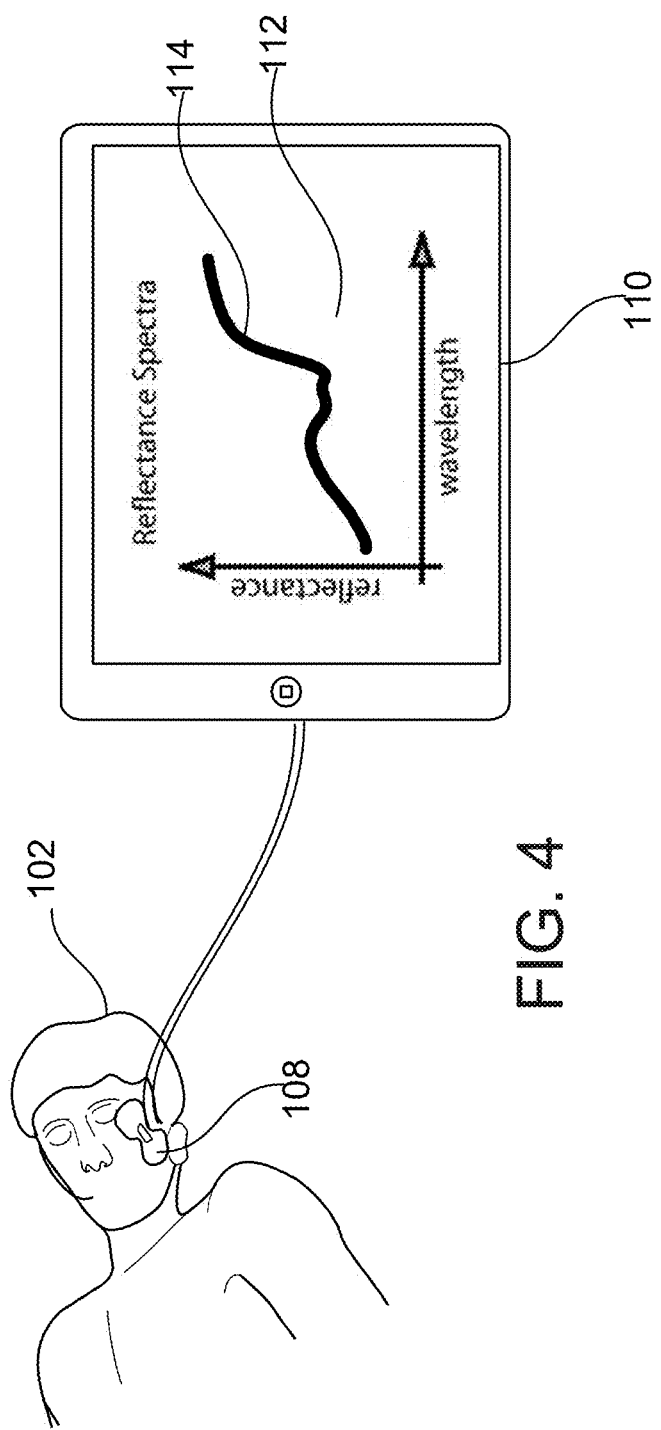
FIG. 4 shows a system for monitoring skin color of a patient based on reflectance or spectra.

FIG. 4 shows a system for analyzing the medical condition of a victim or patient 102. The system includes a colorimeter 108 or other device capable of measuring the color of the skin predominantly of the surface and the near-surface layers down to, and including, the dermal papillae. The colorimeter 108 is configured to obtain a spectra based on an intensity of light reflected primarily from the epidermis and dermal papillae of an individual's skin.

The colorimeter 108 may take the form of a spectrophotometer which generates spectral reflectance/absorbance data, for instance a light source with a optical spectrum extraction element like a diffraction grating and a distributed photon detection element such as a charge-coupled device (CCD) known to those skilled in the art. The spectrophotometer provides a quantitative measurement of the reflection or absorption properties of a material as a function of wavelength. The light source is affixed to the surface of the skin and the angle of incidence is adjusted to provide the majority of the illumination in the outermost layers of the skin—the dermal papillae and the epidermis. In one embodiment, the light source is collimated and provided at an angle of incidence of between about 30 degrees and about 60 degrees (e.g., about forty-five degrees). The optical spectrum extraction element may also be positioned such that the optical path is at a different incidence angle from that of the light source in order to minimize the effect of surface reflections.

The sensing element of the colorimeter may take the form of a wavelength selection optical element such as a liquid crystal tunable filter (LCTF) or acousto-optical tunable filter (AOTF), known to those skilled in the art of color sensing. The colorimeter 108 may also take the form of a light source and a camera, using a lens and CCD such as that found in any commercial digital camera or smart phone such as an iPhone (Apple Computers). In such embodiments, the color information from the CCD includes luminance information for each of multiple colors (e.g., red, green and blue) collected at pixels in the CCD. The colorimeter may be a device such as the Konica-Minolta Model CM-700d (Japan). The software used for analysis of the color may incorporate an algorithm that measures skin pigmentation separately from blood using an index such as the melanin index, as well as the erythema index—the redness of the skin separated from that of melanin, known to those skilled in the art. If the colorimeter takes the form of a light source, lens and image CCD like on an iPhone, the colorimetric data be in the form of the three data pixel elements used in commercial CMOS color imaging sensors and averaged for some specified region of the image generated.

Figure 5:
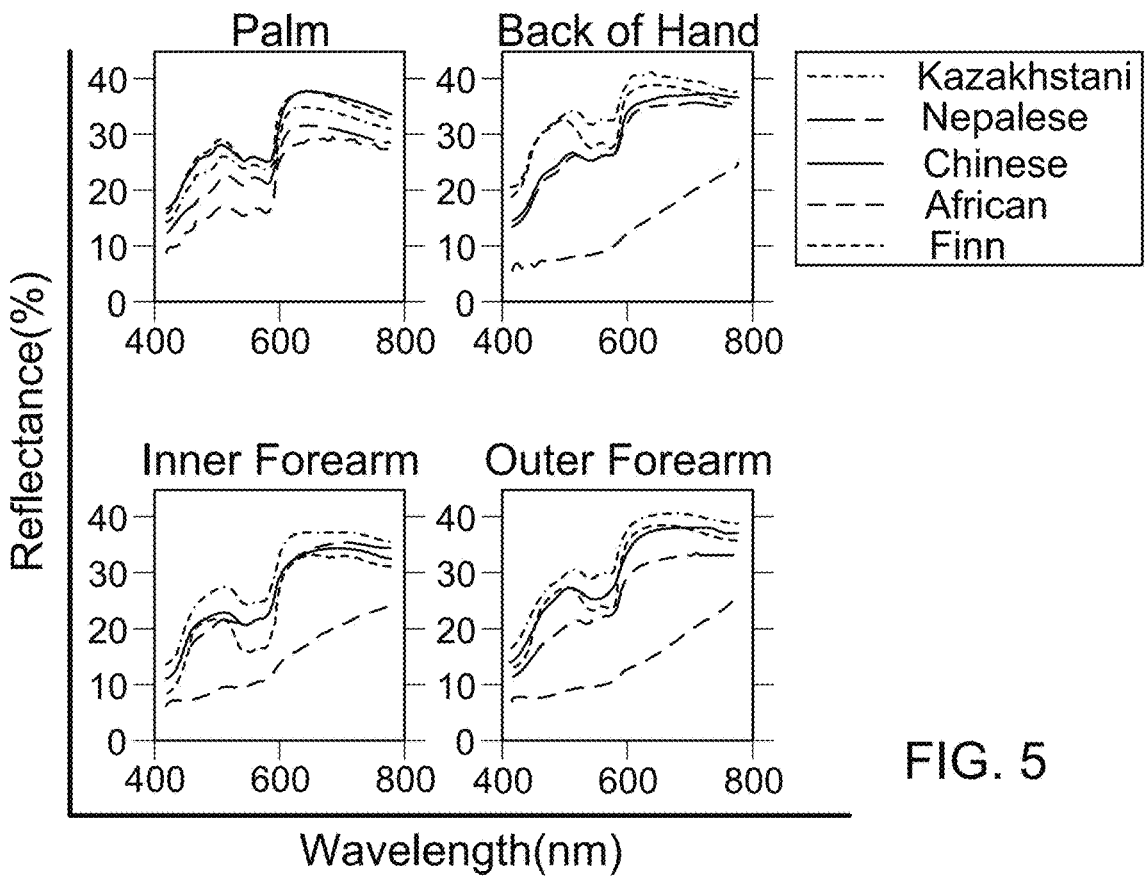
FIG. 5 shows exemplary graphs of skin pigment variation across race and ethnicities.

While FIG. 4 shows the sensor positioned on a patient's cheek, in some examples, the sensor may be positioned on the palm of the patient's hand where skin pigmentation differences are minimal across a wide variety of test subjects (see FIG. 5 which shows exemplary reflectance versus wavelength graphs for multiple, different races/ethnicities at different locations on the individual. As seen in FIG. 5, the reflectance is most similar across the different races/ethnicities for measurements taken on the palm). The palm, positioned on the periphery, will also be more sensitive to vasoconstriction and thus to changes in the patient's underlying physiologic status.

Figure 9:
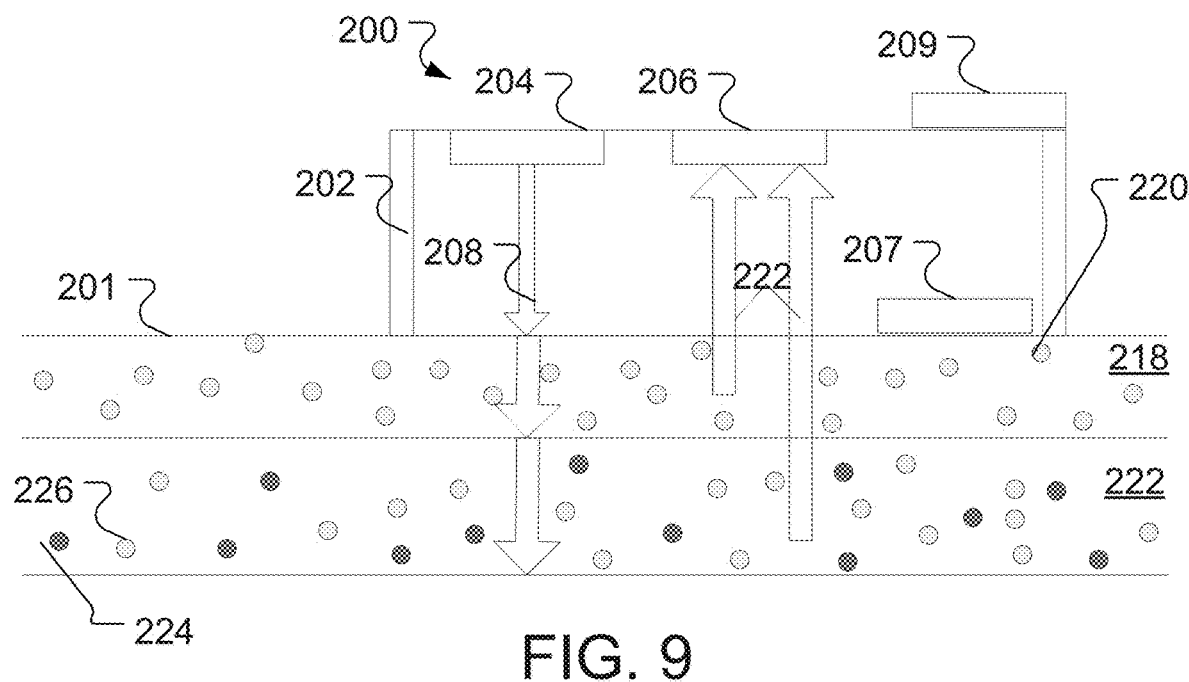
FIG. 9 is a diagram of a colorimeter during analysis of skin.

As shown in FIG. 9, the colorimeter 200 may be composed of skin-attachable element containing the broadband light source 204, such as a "white" LED, a optical sensor 206 and drive electronics located in a band-attached electronic housing attached around the patient's wrist and a fiber optic element for transmitting the light reflected from the skin under the skin-attachable element back to the sensor electronics located in the band-attached housing. It is understood that "band attached" can mean attaching to the patient's body via cloth, adhesive or any other mechanical means. It may also be attached at the wrist, forearm, elbow, or anywhere else on the arm.

The band attached electronics may process the light to produce the spectrographic information as well as any other colorimetric information, it may also just transmit the raw sensor data or spectrographic information back to a more central processing element that may either be located on the patient's body such as a LifeVest wearable defibrillator (ZOLL Medical, Pittsburgh Pa.) or the X-Series defibrillator (ZOLL Medical, Chelmsford Mass.) located on a crash cart or bedside to the patient. The data may also be transmitted by wire connection to the Lifevest. The data may also be transmitted back to a portable computing device like an iPhone or iPad or other computing device. The data may also be transmitted wirelessly to a wireless router and server on a wireless network such as a hospital data system, for instance transmitting the data back to a central station monitoring system. The data may also be transmitted back via a cellular connection to a server or to a physician or other health care provider.

In some examples, the device may contain a temperature sensor or more than one temperature sensor. For instance, it can be desirable to calibrate out the effects of skin temperature on vasodilation. Two temperature probes 207, 209 may be provided: the first temperature probe 207 is located within the housing at a location to place the probe against the surface of the skin and the second temperature probe 209 is located on the outside of the sensor (e.g., on the outer-surface of the housing) and measures air temperature. Since there is wide variation in the effects of temperature on vasodilation in the various regions of the body where the probe may be placed, ideally the effects of temperature can be calibrated with each patient in advance.

As opposed to devices like pulse oximeters, where the wavelengths of light emitted by light source 204 and detected by sensor 206 are configured to detect the presence or absence of blood within the skin disposed proximate to the sensor 206, with the current device, the light emitted is a broad spectrum, AKA "white light" so that the color of the skin can be properly measured. For example, the light emitted by light source 204 and detected by sensor 206 can span at least 200 nm of wavelengths (e.g., at least 200 nm, at least 300 nm, at least 350 nm, at least 500 nm). In one particular example, the light emitted by light source 204 and detected by sensor 206 include wavelengths from about 380 nm to about 780 nm. This range can be extended outside of the visible region, for instance to include wavelengths down to 240 nm to measure effects of NAD and/or to wavelengths as long as 1000 nm. In some additional examples, the light emitted by light source 204 and detected by sensor 206 can include a smaller range of wavelengths from about 450 nm to 700 nm.

The colorimeter may incorporate algorithms for converting the spectrographic information to color scale information. There are various color scales used for describing the color of objects. They are often 3-dimensional scales that decompose the color into, for example, attributes of hue, lightness, and saturation. Examples of such 3-dimensional scales include the XYZ, Munsell and Lab color spaces.

In general, a Lab color space is a color-opponent space with dimension L for lightness and a and b for the color-opponent dimensions, based on nonlinearly compressed CIE XYZ color space coordinates. Lightness (sometimes called value or tone) is a property of a color, or a dimension of a color space, that reflects the subjective brightness perception of a color along a lightness-darkness axis.

Various Lab-type color spaces include the Hunter 1948 L, a, b color space which includes the dimensions of L, a, and b. and the CIE 1976 (L*, a*, b*) color space (or CIELAB). The difference between Hunter and CIE color coordinates is that the CIE coordinates are based on a cube root transformation of the color data, while the Hunter coordinates are based on a square root transformation.

Both spaces are derived from the "master" space CIE 1931 XYZ color space, which can predict which spectral power distributions will be perceived as the same color (see metamerism), but which is not particularly perceptually uniform. Both "Lab" color spaces provide a space which can be computed via simple formulas from the XYZ space, but is more perceptually uniform than XYZ. Both Lab spaces are relative to the white point of the XYZ data they were converted from. Lab values do not define absolute colors unless the white point is also specified (or assumed to follow a standard such as the CIE standard illuminant D50).

The lightness correlate in CIELAB is calculated using the cube root of the relative luminance.

The L*a*b* color space includes all perceivable colors which means that its gamut exceeds those of the RGB and CMYK color models. It is believed that the L*a*b*-model can provide device independence, e.g., the colors are defined independent of their nature of creation or the device they are displayed on. Further information about the Lab color space can be found, for example, at http://en.wikipedia.org/wiki/Lab_color_space.

Figure 6:
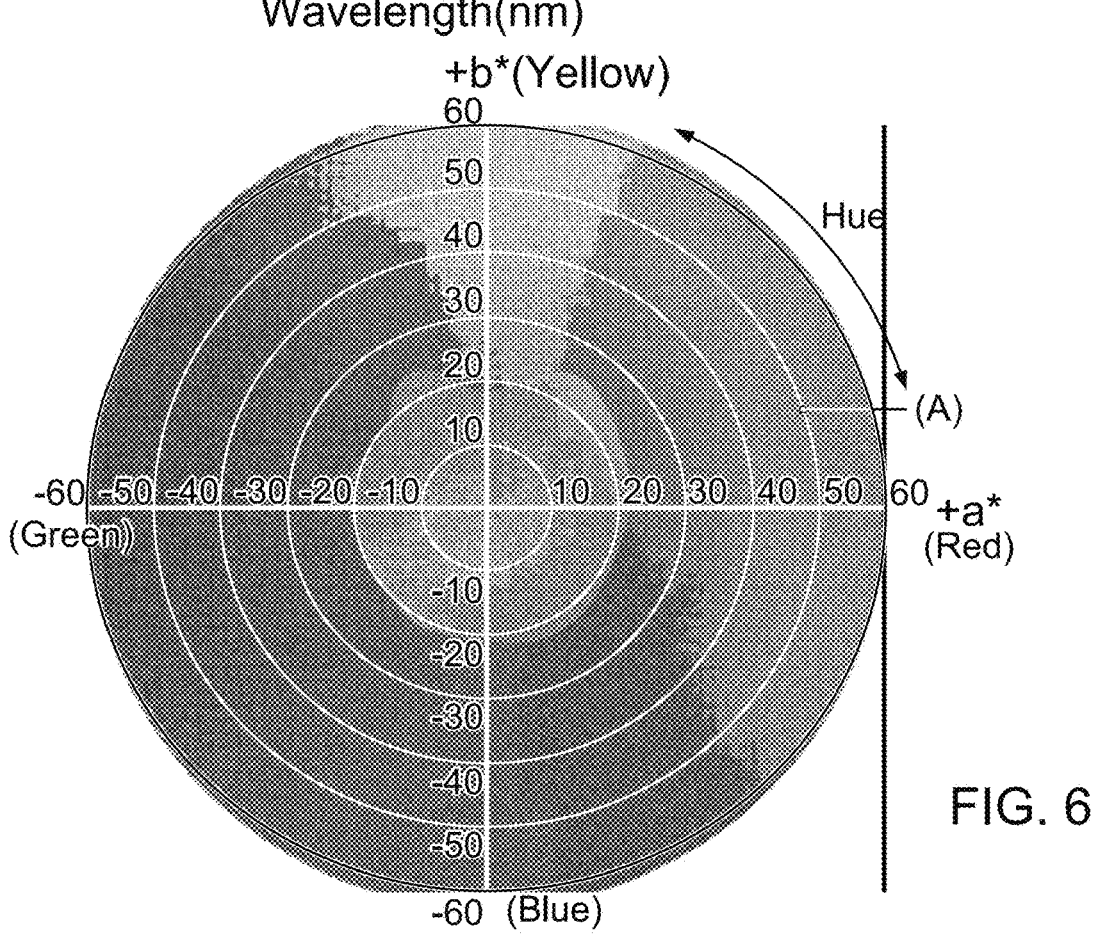
FIG. 6 shows an exemplary diagram of the L*a*b* color space.
Figure 7:
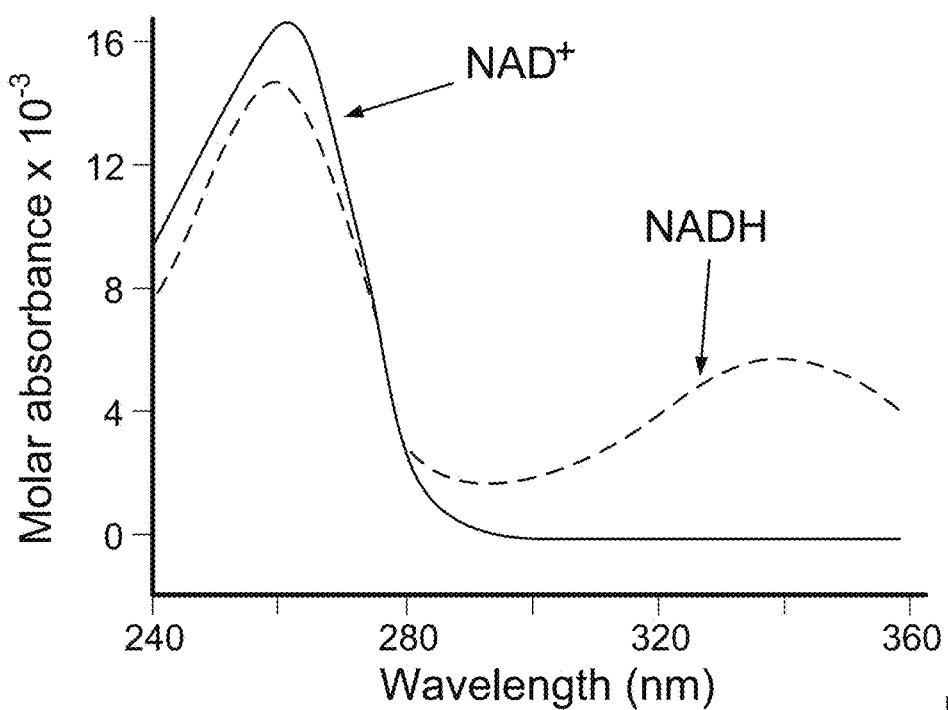
FIG. 7 is a graph of exemplary spectral absorbance data.

In the L*a*b* color space, L* indicates lightness and a* and b* are the chromaticity coordinates. FIG. 6 (from "Precise Color Communication", pg 11, Konica Minolta brochure 2003, downloaded from http://www2.konicaminolta.eu/eu/Measuring/pcc/en/index.html) shows the a*, b* chromaticity diagram. In this diagram, the a* and b* indicate color directions: +a* is the red direction, −a* is the green direction, +b* is the yellow direction, and −b* is the blue direction. The center is achromatic; as the a* and b* values increase and the point moves out from the center, the saturation of the color increases. In some embodiments, the light source and sensor may also emit/detect wavelengths not in the visible portion of the spectrum. For instance, both NAD+ and NADH strongly absorb ultraviolet light because of the adenine. For example, as shown in FIG. 7, peak absorption of NAD+ is at a wavelength of 259 nanometers (nm), with an extinction coefficient of 16,900 M-1 cm-1. NADH also absorbs at higher wavelengths, with a second peak in UV absorption at 339 nm with an extinction coefficient of 6,220 M-1 cm-1. This difference in the ultraviolet absorption spectra between the oxidized and reduced forms of the coenzymes at higher wavelengths enables measurement of the conversion of one to another in enzyme assays based on a measurement of the amount of UV absorption at 340 nm using a spectrophotometer. In the Lab color space, the spectral range is from 380 nm to 780 nm. This range can be extended outside of the visible region, for instance to include wavelengths down to 240 nm to measure effects of NAD, or to wavelengths as long as 1000 nm to look at near infrared optical effects. Adjustments to the color matching functions would be made to sense this broader spectral range and maintain a tri-stimulus measure. A new color space can be created to account for the broader wavelength range. The color space may still be a tri-stimulus space, such as the CIE color-matching functions modified for the broader spectral range, by just changing the maximum and minimum wavelengths, or there might be additional color-matching functions such as the functions shown in FIG. 7 to distinguish between the oxidized and reduced forms of NAD resulting in a penta-stimulus or other higher-dimensional color space.

Figure 8:
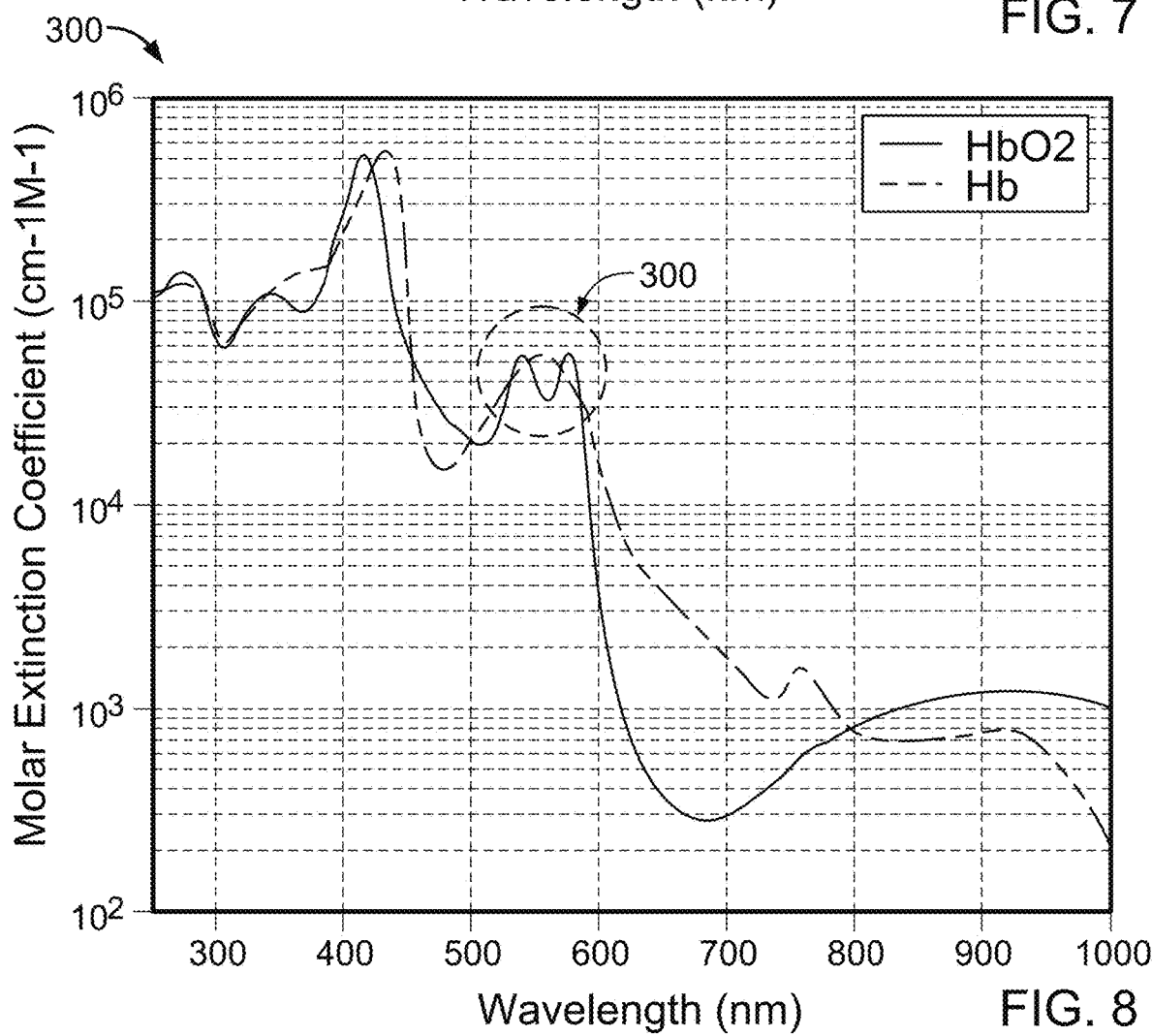
FIG. 8 is a graph of exemplary spectral reflectance data.

Information such as reflectance or absorbance spectrum or color scale values and graphs (RAS/CSVG) is displayed on a user interface 110 (See FIG. 1). Reflectance or absorbance spectrum (RAS) such as that shown in FIG. 7 are not well suited to measuring the paleness or relative paleness or pallor of the skin, and in fact, the pallor of a patient's skin may change radically, becoming much more pale and indicating an impending serious medical condition, but the blood oxygenation of the patient's skin may have changed very little. In this case, the relative levels of Hb and Hb0$_2$ will remain nearly constant while the spectra of these two components diminishes relative to the overall spectra of the other element of the skin. Therefore, it is believed to be advantageous to measure the shifts in color of the patient's skin using color scales other than standard plotting spectrographs with amplitudes plotted as function of frequency such as in FIG. 8 (FIG. 8 shows absorption curves for oxygenated (HbO2) and deoxygenated blood (Hb)).

As noted above, it is believed that the L*a*b* scale described above provides an easier measure of pallor. Lower values of a* and b* indicate decreasing saturation and increasing values of L* indicate increasing lightness.

Considering the color of the skin to lie on the a*-b* plot of FIG. 6, the change in pallor can be calculated by a processor as the vector difference between the current skin color and a previously measured color. In some particular embodiments, the change in pallor can be estimated from the equation:

$$\Delta P = [(a^*_2)^2 + (b^*_2)^2]^{1/2} - [(a^*_1)^2 + (b^*_1)^2]^{1/2},$$

Where "$\Delta P$", the Pallor index, is the change in magnitude of the vectors from $(a^*_1, b^*_1)$ to $(a^*_2, b^*_2)$. These are considered radial vectors generated by the two points in the Lab color space and the origin of the a-b plot, which is grey, i.e. without color. The Pallor index may also be configured to only use the a* values.

The display can include a graph 112 that includes reflectance versus wavelength data 114 or color scale values, erythema index, color scale graphs or pallor index. In the example of FIG. 1, the computing device is in the form of a touchscreen tablet that includes a graphical display by which to report information to the emergency medical technician, and may have an input mechanism such as a keyboard or a touchscreen by which the emergency medical technician may enter data into the system. In addition, or alternatively, the system may provide verbal instructions to the medical professional, such as by telling the medical professional whether the patient's condition is improving or deteriorating.

The display can also include a trend plot of the time course of the patient's skin color, as plotted on, for instance, the Lab scale. The trend plot may also be a plot of any single measure of the color plotted individually or with other color-related data elements, such as Pallor index.

The data generated by the colorimeter 108 can be used during a diagnosis because the light reflected from the target tissue can yield diagnostic information based on the composition and structure of the tissue.

The colorimeter 108 is shown in a deployed state and is connected to the victim 102. The colorimeter 108 serves as a patient monitor by analyzing colorimetric information such as shifts in coloration of the patient 102. For example, as shown here, colorimeter 108 has been applied to the bare cheek of the victim 102 and has been connected to the tablet computer, so that information can be relayed to the medical professional. In general, the colorimeter 108 can be applied to various locations on the victim's skin, such as the victim's face, forehead, lips, ear, and/or the back or palm of the patient's hand. As mentioned previously, at least some portion of the colorimeter 108 may be affixed to the hand, wrist, arm or shoulder of the patient, the patient affixed portion containing the light source and light sensing spectrographic element.

FIG. 9 shows a colorimeter 200 in contact with a surface 201 of a patient's skin. The colorimeter 200 includes a housing 202 that contains a light source 204 and a sensor 206. In some examples, the light source 204 can be a light emitting diode (LED) and the sensor 206 can include a diffraction grating placed in front of the CMOS sensor where each pixel in the CMOS sensor detects a range of the light spectrum emitted by the light emitting diode. The housing 202 is configured to prohibit light from external light sources, such as ambient light, from entering the sensor 206. As such, the light measured by sensor 206 is reflected light originating from the light source 204.

During use, the colorimeter 200 is placed in contact with a patient skin 201 such that ambient light does not enter the housing 202 of the colorimeter. Then light 208 is emitted from the light source 204 and directed toward the patient's skin 201. A portion of the light is absorbed by the melanin 220 in the epidermis 218 and additional portions of the light are absorbed by the oxyhemoglobin 226 and deoxyhemoglobin 224 and layer 222. Light that is not absorbed (e.g., the reflected light 222) impinges upon the surface of the sensor 206. Thus, sensor 206 collects spectral reflectance/absorbance information which can be used to determine colorimetric information used to assess status of the patient. For example, a computing device such as a processor can receive the reflectance/absorbance information and determine the colorimetric information based on the Lab or L*a*b* scales described herein.

FIG. 8 shows a graph 300 of exemplary spectral data of reflectance versus wavelength for multiple different levels of blood content within the skin. In graph 300, the lines each represent a different amount of blood in the skin with the blood content decreasing from the bottom lines to the top. Oxyhemoglobin is the main contributor to adsorption of light by blood and thus an indicator of the level of blood perfusion. Oxyhemoglobin exhibits absorption maxima at 415 nm, 540 nm and 576 nm. Thus, the oxygenated hemoglobin in the blood vessels is responsible for a "W" pattern in the reflectance spectrum (e.g., as seen in region 302). Changes in the spectral reflectance of human skin can be measured to determine increases in reflectance which result from a decrease in the amount of blood circulating in the underlying tissue and/or decreases in reflectance which result from an increase in the amount of blood circulating in the underlying tissue.

When the amount of blood circulating in the tissue falls below a threshold level, a loss of the characteristic 'W' shape (e.g., in the region of about 525-575 nm) occurs because of a decrease in the amount of hemoglobin present which absorbs light strongly over this region. From the color space perspective, this change in the spectrographic characteristics represents a shift in the color coordinates from a more reddish hue to one closer to the color of the underlying tissue in the epidermal layer.

Figure 10:
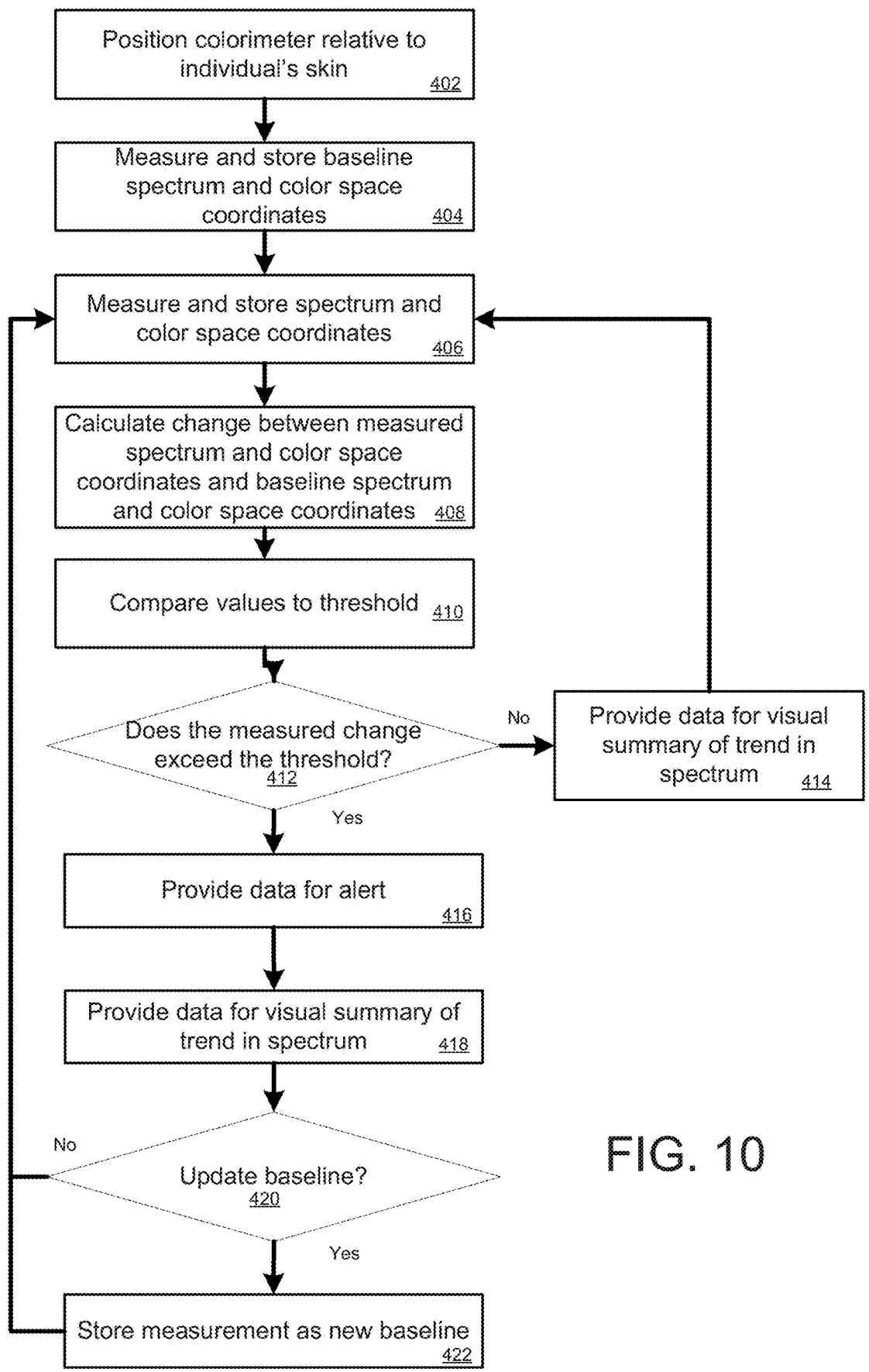
FIG. 10 is a flow chart of a process for providing feedback to a medical professional based on skin colorimetric information.

FIG. 10 shows a flowchart for providing information gathered from spectral reflectance or absorption data to a medical professional.

The process begins with a medical professional or other user placing the colorimeter proximate to the patient's skin (402). For example, the colorimeter can be included in an adhesive patch, which is applied to the patient's skin. In another example the colorimeter can be included in a headband or other wearable unit configured to maintain contact of the colorimeter with the patient's skin. In other examples, the colorimeter can be placed at another predefined location relative to the patient.

After placing the colorimeter proximate to the patient's skin, the system measures and stores color information such as a baseline reflectance or absorbance spectrum or luminance information collected by a charge-coupled device (404) as well as the color scale location in the n-dimensional color space such as Lab. The stored reflectance or absorbance color information such as the spectrum or color scale values and graphs (RAS/CSVG) or luminance information from the CCD device includes measured values for a predefined range of wavelengths as well as the color space coordinates. The baseline reflectance or absorbance color information such as the spectrum and color space coordinates can be used as a comparison point to determine whether later collected spectra and coordinates exhibit a change. Such a change may be indicative of a change in blood perfusion or other patient status such as decreased liver function. In general, the information and measurements described herein can be stored on any memory or computer readable medium including volatile and/or non-volatile memory units such as a floppy disk device, a hard disk device, an optical disk device, or a tape device, a flash memory or other similar solid state memory device, or an array of devices, including devices in a storage area network or other configurations. Subsequent to measuring the baseline reflectance or absorbance color information such as the spectrum and color space coordinates, one or more additional measurements of color information such as another absorbance or reflectance spectrum and color space coordinates or luminance information are measured and stored (406). The system then calculates a difference between the measured color information and the stored baseline color information. For example, the system can calculate a difference between the measured spectrum and color space coordinates and the previously collected baseline spectrum and color space coordinates (408). Differences in the measured RAS/CSVG and the baseline RAS/CSVG are compared to stored threshold values (410) and the system determines whether the measured change exceeds the threshold (412). The system can calculate indices of skin color such as the Erythema index or Pallor index from the color space values. Baseline values can be calculated for these indices and compared to ongoing measures of those indices. The stored threshold values provide a triggering mechanism to alert a user of a change in the measured quantity that may be medically significant. The threshold can be based on a percentage change in the measured signals such as a 10% or 20% change. Viewing the spectral data as a delta from the baseline signal filters out the absorption due to melanin, such that the change in absorption due to increased or decreased blood in the dermal papillae is observed.

If the measured change does not exceed the threshold, the system provides data for visual summary of the spectral information to the user (414), and returns to measuring and storing a new color information such as a new spectrum at the appropriate time (406). For example, the system can automatically collect a new RAS/CSVG at predefined intervals such as every five minutes. The system may also look at absolute values of either the color space values or such indices as the Pallor or Erythmea index and set alert or alarm thresholds based on the absolute values of indices such as these.

The system may also combine multiple skin color measures to calculate a statistical measure of the risk of an impending acute medical event (IAME) such as a cardiac arrest, syncopal episode, traumatic arrest due to such causes as internal bleeding, blunt force trauma, various causes of hypovolemia and heart attack. This combination may take the form of a logistic regression analysis.

The model for simple linear regression is:

$$Y=a+b*X$$

where y is the dependent variable, x is the independent variable, and b is the regression parameter (the intercept and the slope of the line of best fit). The model for multiple linear regression is:

$$Y=a+b_1*X_1+b_2*X_2+\ldots+b_i*X_i$$

The coefficients, $b_i$, for each input parameter, $X_i$, are calculated using statistical methods such as the general linear model to provide a best estimate of the probability of defibrillation success, Y. The variable, Y, may also represent the probability of any therapeutic intervention other than the IAME, for instance chest compressions, ventilations or a metabolic treatment such as epinephrine or other vasopressor or hemodynamic support agent. The General Linear Model (GLM) can estimate and test any univariate or multivariate general linear model, including those for multiple regression, analysis of variance or covariance, and other procedures such as discriminant analysis and principal components. With the general linear model, randomized block designs, incomplete block designs, fractional factorial designs, Latin square designs, split plot designs, crossover designs, nesting, can be explored. The model is:

$$Y = XB + e$$

where Y is a vector or matrix of dependent variables, X is a vector or matrix of independent variables, B is a vector or matrix of regression coefficients, and e is a vector or matrix of random errors.

In multivariate models, Y is a matrix of continuous measures. The X matrix can be either continuous or categorical dummy variables, according to the type of model. For discriminant analysis, X is a matrix of dummy variables, as in analysis of variance. For principal components analysis, X is a constant (a single column of '1's). For canonical correlation, X is usually a matrix of continuous right-hand variables (and Y is the matrix of left-hand variables).

For some multivariate models, it may be easier to use ANOVA, which can handle models with multiple dependent variables and zero, one, or more categorical independent variables (that is, only the constant is present in the former). ANOVA automatically generates interaction terms for the design factor.

After the parameters of a model have been estimated, they can be tested by any general linear hypothesis of the following form:

$$ABC' = D$$

where A is a matrix of linear weights on coefficients across the independent variables (the rows of B), C is a matrix of linear weights on the coefficients across dependent variables (the columns of B), B is the matrix of regression coefficients or effects, and D is a null hypothesis matrix (usually a null matrix).

The coefficients, $b_i$, are calculated using skin color or other measured physiological data collected from a statistically varied population of samples to provide a robust database for accurate model generation.

Regression may also be performed using the logistic function:

$$Y = 100 \left[ 1 - \frac{1}{1 + e^{b_o + \Sigma b_i x_i}} \right]$$

A state transition matrix can be developed using a Markov model and the threshold adjusted as well as different weighting coefficients applied based on the Markov model estimation. In particular, the sequence of medical interventions and patient reactions to treatments is modelled as a hidden Markov model (HMM), defined as a variant of a finite state machine having a set of states, Q, an output alphabet, O, transition probabilities, A, output probabilities, B, and initial state probabilities, Π. The current state is not observable. Instead, each state produces an output with a certain probability (B). Usually the states, Q, and outputs, O, are understood, so an HMM is said to be a triple, $\lambda = (A, B, \Pi)$. Each value of output alphabet, O, can be given a unique threshold and coefficient set.

$A = \{a_{ij} = P(q_j \text{ at } t+1 | q_i \text{ at } t)\}$, where P(a|b) is the conditional probability of a given b, t≥1 is time, and $q_i \in Q$. Informally, A is the probability that the next state is $q_j$ given that the current state is $q_i$.

$B = \{b_{ik} = P(o_k | q_i)\}$, where $o_k \in O$.

Informally, B is the probability that the output is $o_k$ given that the current state is $q_i$.

$\Pi = \{p_i = P(q_i \text{ at } t=1)\}$.

The Forward-Backward and Baum-Welch algorithms are performed on a database to build the HMM. The estimated trajectory, i*_1, . . . , i*_t+1, using algorithms such as these predicts the next likely event, based on the previous sequence.

If the measured change exceeds the threshold, the system provides data to generate an alert that can be presented to the user (416). Exemplary alerts can include visual alerts, audio alerts, or other indicators used to alert a medical professional to the change in the patient's status. The system also provides data for visual summary of the spectral information to the user (418). For example, the information can be displayed on a display device. A continuous or near-continuous risk score of impeding IAME, using such methods as logistic regression may also be presented to user.

After alerting the medical professional to the change in the measured color information such as a spectrum relative to the baseline RAS/CSVG, the system determines whether to update the baseline RAS/CSVG used for future analysis (420). In some situations it may be beneficial to update the baseline RAS/CSVG when the measured values for the patient are trending over time, e.g., the patient condition is improving or worsening. For example, if the patient's condition has deteriorated, continuing to measure against an original baseline may provide less useful information to a medical professional about the current change in the patient's status than could be provided if the baseline was updated. If the system determines to update the baseline, the system stores the current measured RAS/CSVG as the new baseline RAS/CSVG (422) and returns to measuring and storing a new RAS/CSVG (406).

In some examples, it can be beneficial to generate a metric which combines measurements of the skin color with an acuity score based on factors such as heart rate, blood pressure, respiration rate, and/or mental responsiveness. In one particular example, a modified early warning score (MEWS) can be combined with a skin color measurement in order to generate a warning score that is based in part on colorimetric properties of the individual's skin. In some examples, the calculated score can be derived from physiological readings such as systolic blood pressure, heart rate, respiratory rate, body temperature and the information about skin color. In one particular example, the observation, or alertness score from the in MEWS scoring can be replaced by a measurement of colorimetric properties of the individual's skin.

Figure 11:
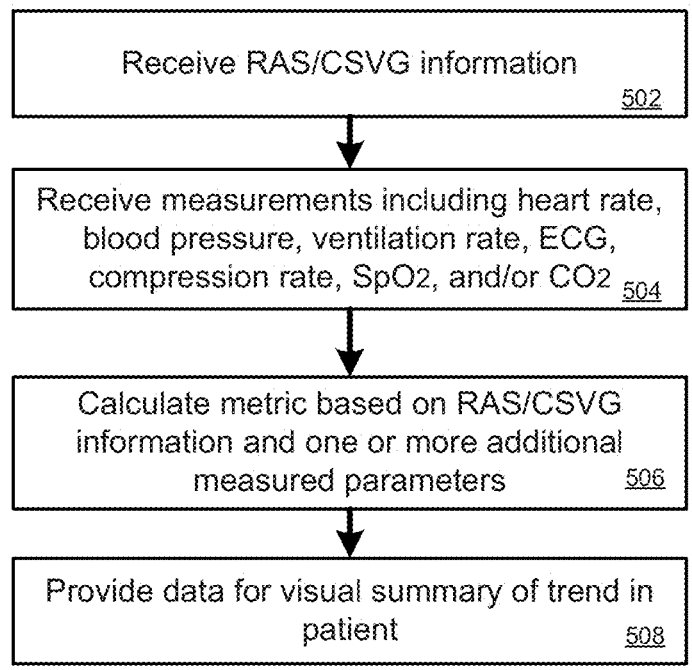
FIG. 11 is a flow chart of a process for generating a metric based on colorimetric information and other measurements.

FIG. 11 shows a flowchart of an exemplary process for calculating a metric based on both RAS/CSVG information and one or more additional measured parameters. The system receives RAS/CSVG information such as RAS/CSVG and/or changes between a current RAS/CSVG and prior/baseline RAS/CSVG (502). The system also receives measurements including one or more of heart rate, blood pressure, ventilation rate, ECG measurements, compression rate, SpO$_2$, and/or CO$_2$ (504). Using both the RAS/CSVG information and the one or more additional the measured parameters, the system calculates a metric indicative of overall patient status (506). The system provides data for visual summary of the trend in the patient based on the calculated metric (508). For example, the system can generate a display that includes a time-based progression of the calculated metric.

Responsiveness is another indicator of patient status. Various scales can be used to assess the responsiveness of a patient. One example is the AVPU scale (an acronym from "alert, voice, pain, unresponsive"), which is a system by which a health care professional can measure and record a patient's responsiveness, indicating their level of consciousness. Another example is the Glasgow Coma Scale, which assesses a patient response in three measures—Eyes, Voice and Motor skills. Systems and methods herein can be used to supplement and/or replace such subjective scales with an objective responsiveness indicator that is based on skin coloration. It is believed that, certain stimuli can generate blushing or other flushing of the face as an involuntary response to the stimuli. These short-term changes of colorimetric skin properties based on the emotional response of the person can be indicative of the responsiveness level of a patient. Thus, RAS/CSVG information gathered by a colorimeter can be used as an objective measurement of responsiveness.

The stimulus may take the form of pressure, such as an air filled bladder that presses against the skin then releases the pressure to look at the changes in skin color. The sensor might incorporate a pressure sensor so that the user is required to press against the adhesive sensor with their hands or fingers and based on the measured pressures, the system automatically measures the RAS/CSVG at maximal pressure and the again at multiple time points after the release of pressure. In one example, the system takes RAS/CSVG readings at approximately 100 millisecond intervals for a period of approximately 10 seconds to look at the time course of the response of the vasculature. Both absolute change in skin color is measured as well as the dynamic properties of the skin color change. Dynamic skin color changes may take the form of rise time (e.g. time from pressure release to 90% of skin color changes), skin color change (%) at 1 second and 3 seconds, etc.

Figure 12:
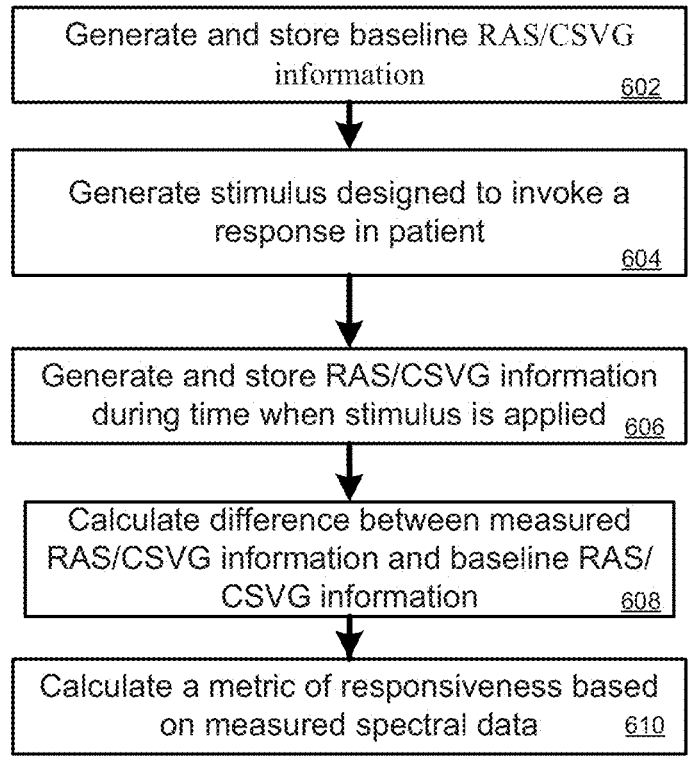
FIG. 12 is a flow chart of a process for calculating a responsiveness metric based on measured colorimetric data.

FIG. 12 shows a flowchart for calculating a metric of responsiveness based on measured RAS/CSVG data. The process begins by generating and storing a baseline spectral reflectance or absorption measurement (602). Subsequent to generating the baseline measurement, the system generates a stimulus that is designed to stimulate a response in a patient (604). For example, an audio input with standard questions that are designed to embarrass or generate another response in the patient can be provided. In another example, a pressure can be applied to the skin. Upon providing the stimulus, the system measures and stores another spectral measurement during the time which the stimulus is applied (606). If the patient is responsive, this stimulus is expected result in a coloration change based on the increased blood flow associated with the emotional response. In order to determine whether the stimuli had the desired effect, the system calculates a difference between the measured RAS/CSVG information in the baseline RAS/CSVG (608), and uses this information to calculate a metric indicative of responsiveness (610). Thus, when the patient does not show the ability to have color modulation in response to the question or stimuli designed to induce the emotional response a medical professional or other caregiver can be notified.

The colorimeters described herein can be incorporated into various types of systems. In some examples, the colorimeters can be used as independent, stand-alone devices. In other examples, the colorimeters can be incorporated into patient management systems such as defibrillators, or other portable devices, and/or incorporated into an ambulance, incorporated into a hospital room or other treatment location.

Figure 13:
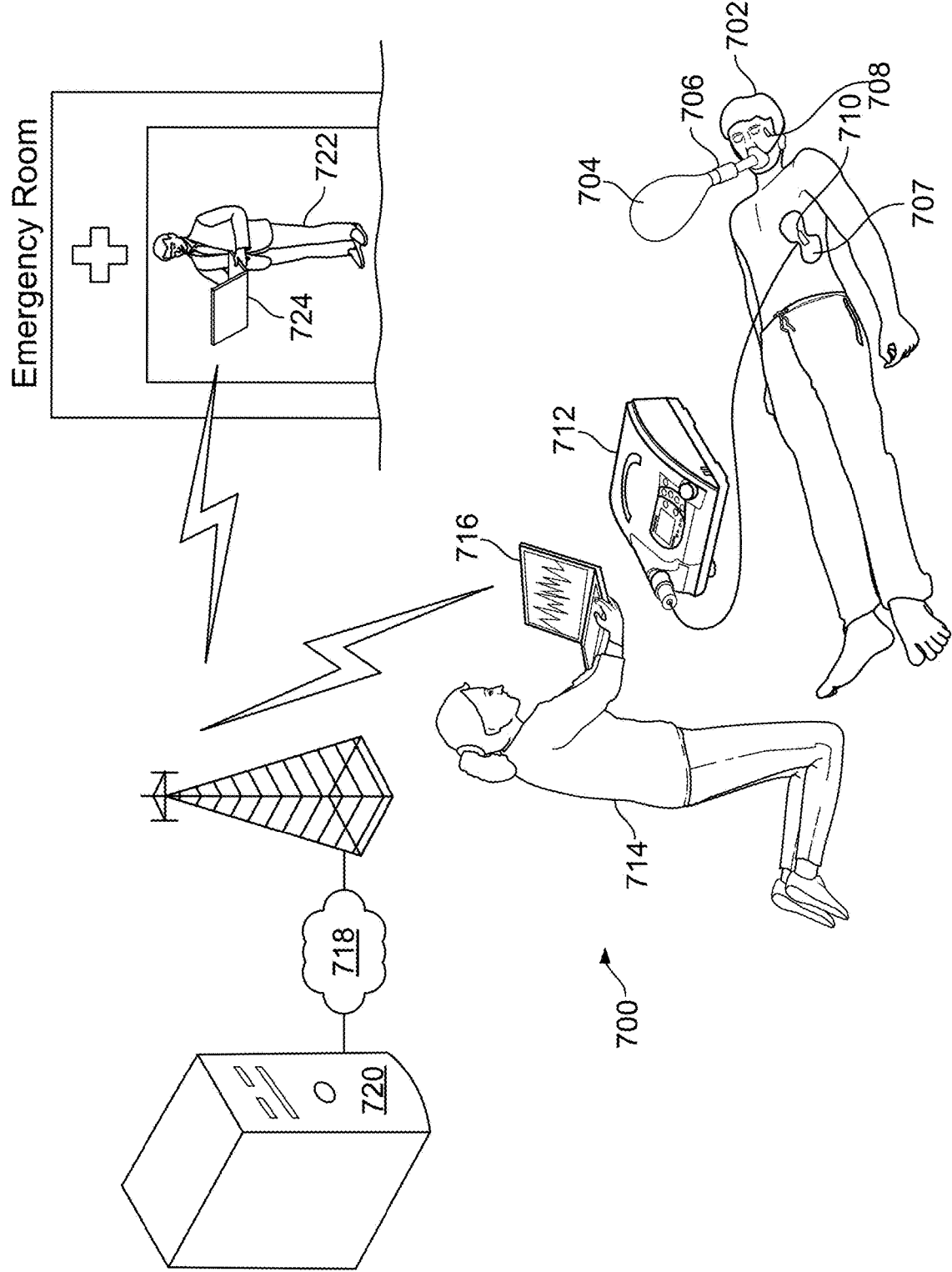
FIG. 13 shows an exemplary system for monitoring a patient.

In one particular example, FIG. 13 shows a system 700 for responding to an emergency medical condition of a victim 702. In general, system 700 includes various portable devices for monitoring on-site care given to a victim 702 of an emergency situation. The various devices may be provided by emergency medical technicians who arrive at the scene and who provide care for the victim 702, such as emergency medical technician 714. In this example, the emergency medical technician 714 has deployed several devices and is providing care to the victim 702 including a colorimeter 708. The emergency medical technician 714 in this example is interacting with a computing device in the form of a touchscreen tablet 716. The tablet 716 may include a graphical display by which to report information to the emergency medical technician 714, including information derived from photo spectrometer 708. A portable defibrillator 712 is shown in a deployed state and is connected to the victim 702. In addition to providing defibrillation, the defibrillator 712 may serve as a patient monitor via a variety of sensors or sensor packages. For example, as shown here, electrodes 707 have been applied to the bare chest of the victim 702 and have been connected to the defibrillator 712, so that electrical shocking pulses may be provided to the electrodes in an effort to defibrillate the victim 702, and electrocardiogram (ECG) signals may be read from the victim 702. The defibrillator 712 may provide feedback in a conventional and known manner to a rescuer, such as emergency medical technician 714.

The defibrillator 712 may communicate through a short range wireless data connection with the tablet 716. The defibrillator 712 can provide to the tablet 716 status information, such as information received through the electrode assembly 707, including ECG information for the victim 702. Also, the defibrillator 712 can send information about the performance of chest compressions, such as depth and rate information for the chest compressions. The tablet 716 can also receive RAS/CSVG data from the colorimeter 708 and/or ventilation data from an airflow sensor 706 provided with a ventilation bag 704. The tablet 716 may display such information (and also other information, such as information from the defibrillator regarding ETCO2 and SPO2) graphically for the emergency medical technician 714. Information provided to the rescuer can be based in part on the RAS/CSVG data collected by colorimeter 708.

A central server system 720 may communicate with the tablet 716 or other devices at the rescue scene over a wireless network and a network 718, which may include portions of the Internet (where data may be appropriately encrypted to protect privacy). The central server system 720 may be part of a larger system for a healthcare organization in which medical records are kept for various patients in the system. Information about the patient 702 may then be associated with an identification number or other identifier, and stored by the central server system 720 for later access. Other users may then access the data in the central server system 720. For example, as shown here, an emergency room physician 722 is operating his or her own tablet 724 that communicates wirelessly, such as over a cellular data network. As such, the physician 722 may review the data from central server system 720. In this manner, the system 700 permits various portable electronic devices to communicate with each other so as to coordinate care that is provided to a victim 702. In addition, the system 700 allows the technician 714 and others to see raw real-time data and derived real-time or historical data about a rescue attempt.

Figure 14A:
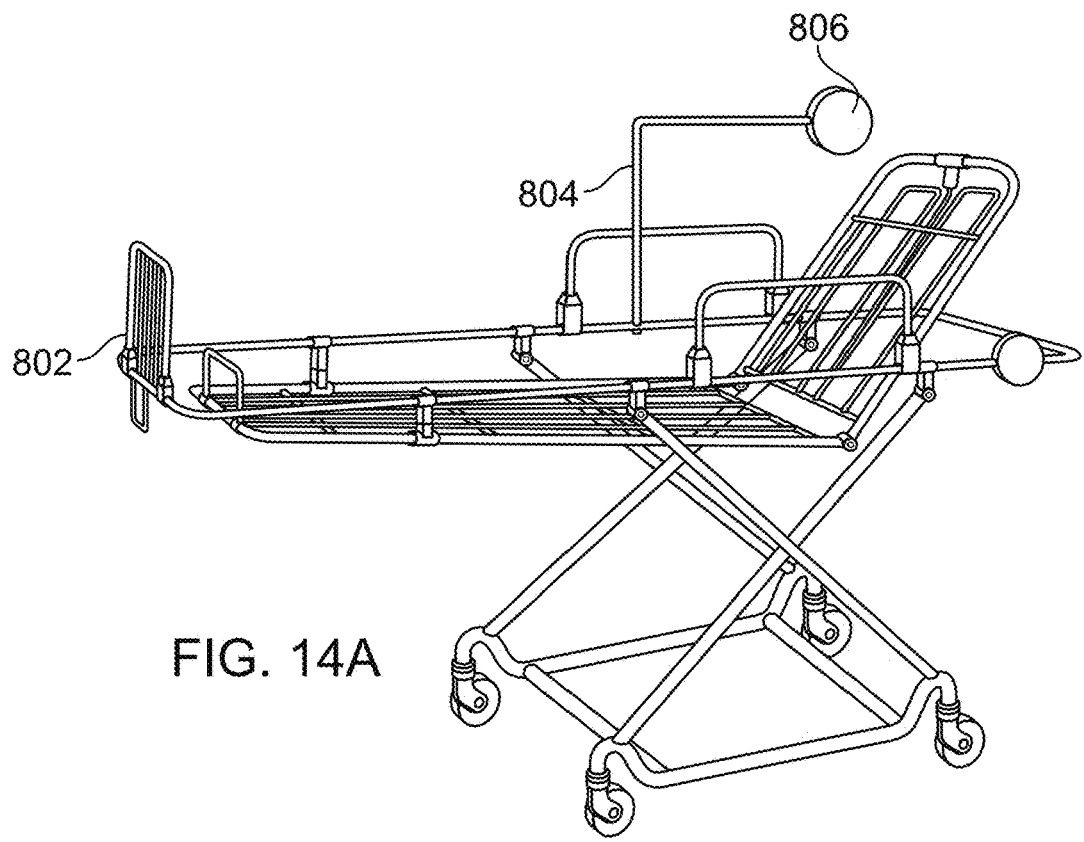
FIG. 14A shows a gurney that includes a colorimeter.

In another example, as shown in FIG. 14A, a colorimeter 806, such as the colorimeters described herein can be attached to a hospital gurney 802 (e.g., a narrow bed on a wheeled frame which may be adjustable in height), such as the type of gurneys that are collapsible for use in ambulances. The gurney 802 can have a rod 804 extending from the frame of the gurney that supports a colorimeter 806. The colorimeter 806 can be positioned such that an image of a patient's head can be gathered by the colorimeter 812.

Figure 14B:
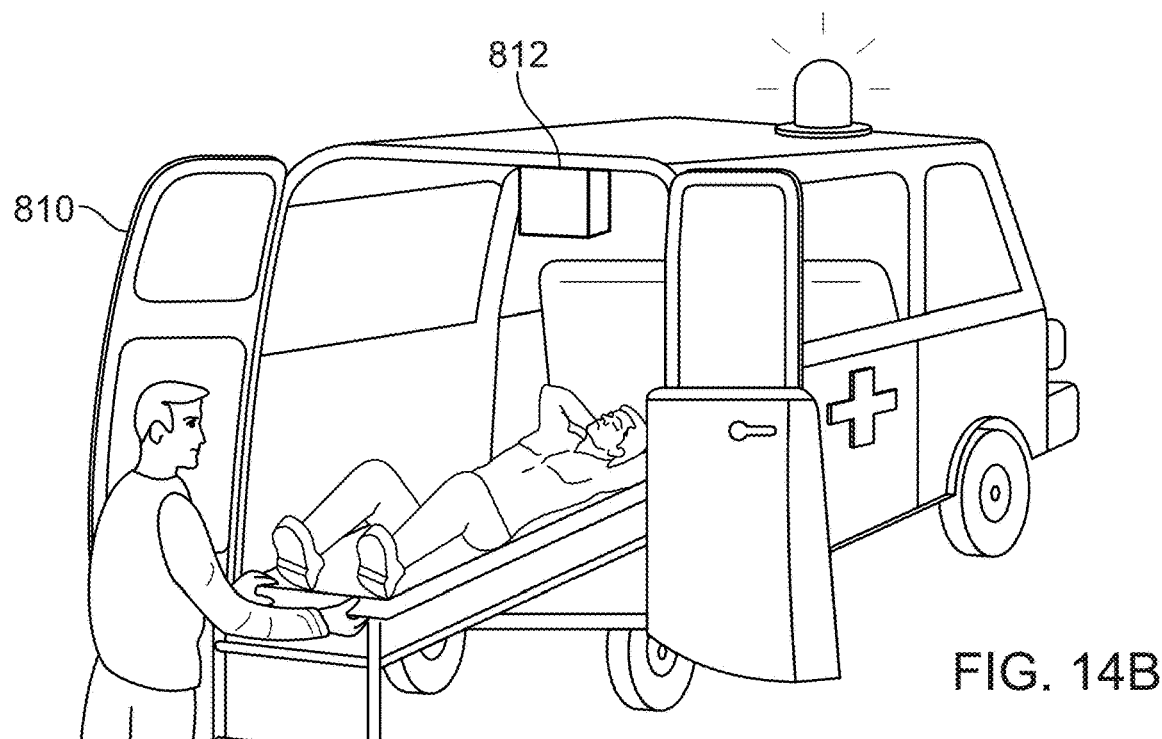
FIG. 14B shows an ambulance that includes a colorimeter.

In another example, as shown in FIG. 14B, a colorimeter 812, such as the colorimeters described herein can be attached to an ambulance 810. For example, the colorimeter 812 can be attached to a roof of the ambulance and positioned such that an image of the patient's head can be gathered from the colorimeter 806.

As noted above, various types of colorimeters can be used to gather the RAS/CSVG data in order to determine patient condition based on skin coloring. Such colorimeters can range from specially designed colorimeters such as those used to measure bilirubin levels, to arrangements that include a light source and a sensor and rely on external processing, to cameras such as those incorporated into many portable devices such as those included in portable telephones (e.g., smart phones such as the iPhone). One such example of a portable device functioning as a colorimeter and used to gather reflectance or absorption spectra is shown in FIG. 9.

Figure 15:
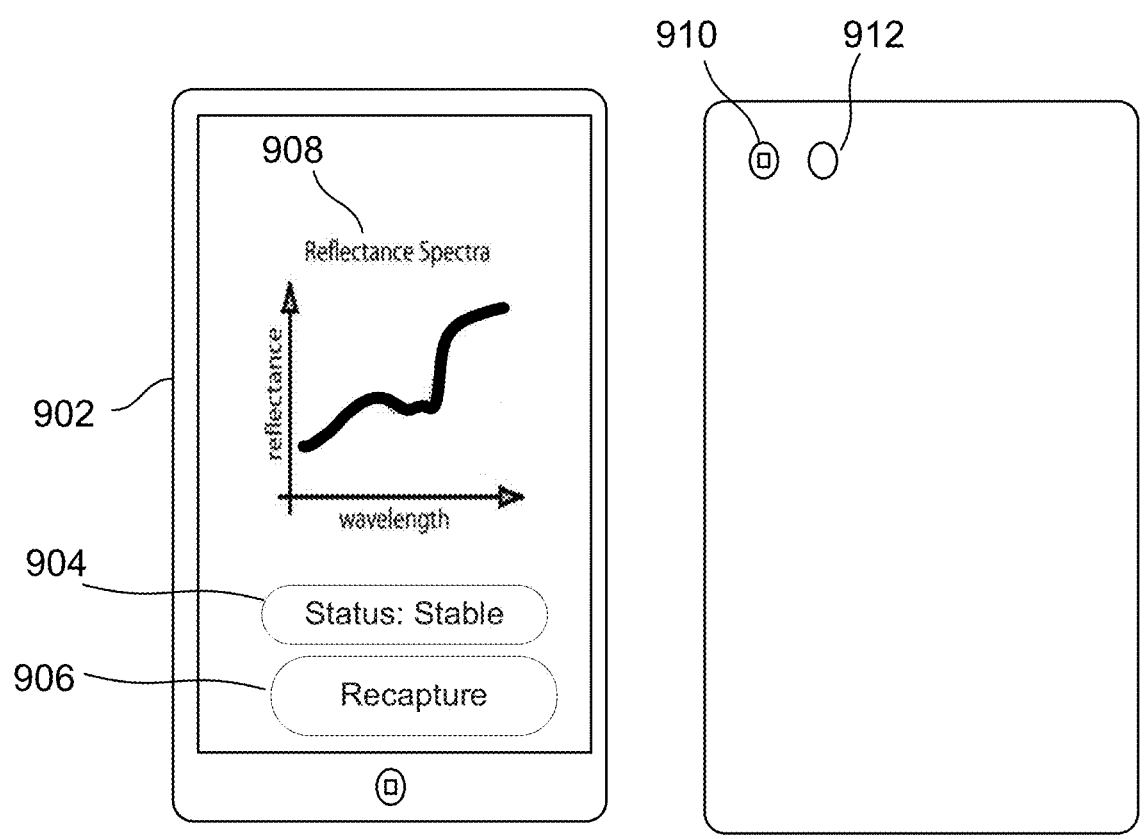
FIG. 15 shows a colorimeter in the form of a portable device.

FIG. 15 shows the front (left) and back (right) sides of a portable telephone 902 that includes a user interface displaying a collected RAS/CSVG 908, a status indicator 904, and a capture/recapture button 906. When a user selects capture/recapture button 906, the portable telephone 902 activates a light source 912 of the device. For example, the portable telephone 902 can activate the flash for the camera of the portable device 902. While the flash has been activated, the portable device 902 captures an image of the patient's skin using a camera 910. Thus, the portable telephone 902 can generate the reflectance/absorption data as described herein. The RAS/CSVG data collected by camera 910 can be analyzed using a processor of the portable telephone 902 to provide feedback to the operator of the telephone.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented method for use with a defibrillator comprising a memory, the method comprising:
    obtaining color information from one or more sensors of a colorimeter based on an intensity of light reflected from an epidermis and dermal papillae of a skin of an individual, the colorimeter coupled with the defibrillator;
    analyzing the color information to determine colorimetric properties of the individual's skin, wherein determining the colorimetric properties includes measuring spectral absorption of the individual's skin;
    applying a color space to the measured spectral absorption of the individual's skin;
    measuring a first set of coordinates in the color space based on the measured spectral absorption of the individual's skin;
    measuring a second set of coordinates in the color space based on the measured spectral absorption of the individual's skin;
    estimating a color index, at least in part, by calculating a change in magnitude between a first vector comprising the first set of coordinates and a second vector comprising the second set of coordinates;
    retrieving, from the memory, a previously estimated baseline color index calculated as a change between two sets of colorimetric properties of the individual's skin;
    determining whether the color index exceeds the baseline color index according to a threshold;
    sensing, via one or more sensors coupled with the defibrillator, one or more additional physical parameters of the individual including one or more of blood pressure, end tidal carbon dioxide (EtC02), blood oxygen saturation (Sp02), mental responsiveness, ventilation rate, and ECG measurements;
    calculating, where the color index exceeds the baseline color index by the threshold, a risk score that provides a measure of the risk of an impending acute medical event for the individual based at least in part on the color index and the one or more additional physical parameters of the individual;
    displaying on an output device a visual summary that includes the calculated risk score to provide an indication of a likelihood of an impending acute medical event for the individual; and
    generating, on the output device, an alert in response to whether the calculated risk score is indicative of an impending acute medical event for the individual.

2. The method of claim 1, wherein the color space is a Lab color space.

3. The method of claim 1, wherein the color space comprises a color space having higher dimensionality than three and having associated stimulus functions.

4. The method of claim 3, wherein the color space comprises a quadrastimulus color space.

5. The method of claim 3, wherein the color space comprises a pentastimulus color space.

6. The method of claim 3, wherein the stimulus functions comprise stimulus functions configured to enhance detection of an underlying physiologic state.

7. The method of claim 6, wherein the underlying physiologic state comprises detection of NAD and NADH.

8. The method of claim 1, wherein the defibrillator comprises a wearable defibrillator.

9. The method of claim 1, further comprising:
obtaining baseline colorimetric properties based on an intensity of light radiation reflected from the individual's skin, wherein obtaining the baseline colorimetric properties is in addition to the measured first and second sets of coordinates; and
estimating the baseline color index at least in part from the baseline colorimetric properties.

10. The method of claim 9, further comprising:
updating the baseline colorimetric properties color index where the color index exceeds the baseline color index by the threshold.

11. The method of claim 1, wherein calculating a risk score provides a measure of the risk of one or more of a cardiac arrest, syncopal episode, traumatic arrest due to such causes as internal bleeding, blunt force trauma, various causes of hypovolemia and heart attack.

12. The method of claim 1, further comprising determining whether the risk score exceeds an established threshold, and wherein generating the alert comprises providing a warning indicating the risk score has exceeded the established threshold.

13. The method of claim 1, wherein obtaining the color information further comprises:
obtaining baseline colorimetric properties based on an intensity of light radiation reflected from the individual's skin, wherein obtaining the baseline colorimetric properties is in addition to the measured first and second sets of coordinates;
applying a stimulus configured to produce a change in the colorimetric properties of the individual's skin; and
obtaining one or more additional measurements of the colorimetric properties at times selected to capture changes in the colorimetric properties of the individual's skin based on the applied stimulus.

14. The method of claim 13, wherein applying the stimulus comprises applying a pressure to the individual's skin.

15. The method of claim 13, wherein applying the pressure to the individual's skin comprises applying the pressure using an air filled bladder that presses against the skin then releases.

16. The method of claim 13, wherein applying the stimulus comprises providing an audio stimulus.

17. The method of claim 13, wherein applying the stimulus comprises stimulating skin with electricity.

18. The method of claim 13, wherein applying the stimulus comprises applying a stimulus configured to generate a pain sensation.

19. The method of claim 13, wherein applying the stimulus comprises providing audio signal or voice generated signal configured to elicit a response.

20. The method of claim 1, wherein the color information comprises a spectra.

21. The method of claim 20, wherein the spectra comprises an absorption spectra for wavelengths between 500 and 600 nm.

22. The method of claim 20, wherein the spectra comprises a reflectance spectra for wavelengths between 500 and 600 nm.

23. The method of claim 1, wherein the color information comprises luminance information for each of multiple colors.

24. The method of claim 1, wherein the color information comprises luminance information for red, green and blue components collected by a charge-coupled device (CCD).

25. The method of claim 1, wherein generating the risk score further comprises combining the determined colorimetric properties with at least one of heart rate, blood pressure, respiration rate, and mental responsiveness.

26. The method of claim 1, wherein analyzing determining the colorimetric properties comprises measuring spectral absorption and filtering out melanin contribution to the spectral absorption.

27. The method of claim 26, wherein the analyzing of the color information includes analyzing ranges of wavelengths and identifying shifts in measured spectral absorption, the shifts in the measured spectral absorption being indicative that a medical status of the individual is worsening.

28. The method of claim 1, wherein the color space comprises is an XYZ color space.

29. The method of claim 1, wherein the color index includes a pallor index.

30. The method of claim 1, wherein the first vector and the second vector comprise radial vectors.

31. The method of claim 1, wherein the threshold is 10%.

32. The method of claim 1, wherein the threshold is 20%.

33. A system for determining information about an individual based on colorimetric properties of a skin of the individual, the system comprising:
a defibrillator comprising a memory storing a baseline color index and configured to provide information regarding a medical condition of the individual;
a colorimeter, coupled with the defibrillator, that includes one or more sensors and configured to measure color information based on an intensity of light reflected from an epidermis and dermal papillae of the individual's skin, wherein the one or more sensors of the colorimeter measure spectral absorption of the individual's skin;
one or more sensors, coupled with the defibrillator, and configured to measure one or more additional physical parameters of the individual including one or more of blood pressure, end tidal carbon dioxide (EtC02), blood oxygen saturation (Sp02), mental responsiveness, ventilation rate, and ECG;
a processor communicatively coupled with the defibrillator and configured to:
analyze the color information to determine the colorimetric properties of the individual's skin,
apply a color space to the measured spectral absorption of the individual's skin;
measure a first set of coordinates in the color space based on the measured spectral absorption of the individual's skin;
measure a second set of coordinates in the color space based on the measured spectral absorption of the individual's skin;
estimate a color index, at least in part, by calculating a change in magnitude between a first vector comprising the first set of coordinates and a second vector comprising the second set of coordinates;

retrieve, from the memory, a previously estimated baseline color index calculated as a change between two sets of colorimetric properties of the individual's skin;
determine whether the color index exceeds the baseline color index according to a threshold; and
calculate, where the color index exceeds the baseline color index by the threshold, a risk score that provides a measure of the risk of an impending acute medical event for the individual based at least in part on the color index and the one or more additional physical parameters of the individual; and
an output device including a display configured to display a visual summary that includes the calculated risk score to provide an indication of a likelihood of an impending acute medical event for the individual,
wherein the output device further configured to generate an alert in response to whether the calculated risk score is indicative of an impending acute medical event for the individual.

34. The system of claim 33, wherein the color space comprises a Lab color space.

35. The system of claim 33, wherein the color space comprises a color space having higher dimensionality than three and having associated stimulus functions.

36. The system of claim 35, wherein the color space comprises a quadrastimulus color space.

37. The system of claim 35, wherein the color space comprises a pentastimulus color space.

38. The system of claim 35, wherein the stimulus functions comprises stimulus functions configured to enhance detection of an underlying physiologic state.

39. The system of claim 38, wherein the underlying physiologic state comprises detection of NAD and NADH.

40. The system of claim 33, wherein the defibrillator comprises a wearable defibrillator.

41. The system of claim 33, wherein the processor is further configured to:
cause the colorimeter to obtain baseline colorimetric properties based on an intensity of light radiation reflected from the individual's skin, wherein the obtained baseline colorimetric properties are obtained in addition to the measured first and second sets of coordinates; and
estimate the baseline color index at least in part from the baseline colorimetric properties.

42. The system of claim 41, wherein the processor is further configured to update the baseline colorimetric properties where the color index exceeds the baseline color index by the threshold.

43. The system of claim 42, wherein the processor is further configured to determine whether the risk score exceeds an established threshold, and provide a warning based on the risk score exceeding the established threshold.

44. The system of claim 33, wherein the risk score provides a measure of a risk of one or more of a cardiac arrest, syncopal episode, traumatic arrest due to such causes as internal bleeding, blunt force trauma, various causes of hypovolemia and heart attack.

45. The system of claim 33, wherein the processor is further configured to obtain the color information by:
obtaining baseline colorimetric properties based on an intensity of light radiation reflected from the individual's skin, wherein the obtained baseline colorimetric properties are obtained in addition to the measured first and second sets of coordinates;
applying a stimulus configured to produce a change in the colorimetric properties of the individual's skin; and
obtaining one or more additional measurements of the colorimetric properties at times selected to capture changes in the colorimetric properties of the individual's skin based on the applied stimulus.

46. The system of claim 45, wherein the processor is further configured to analyze the colorimetric properties by:
comparing the obtained colorimetric properties with the obtained baseline colorimetric properties to determine an amount of change between the obtained colorimetric properties and the baseline colorimetric properties in response to the applied stimulus.

47. The system of claim 33, wherein the color information comprises an absorption spectra for wavelengths between 500 and 600 nm.

48. The system of claim 33, wherein the color information comprises a reflectance spectra for wavelengths between 500 and 600 nm.

49. The system of claim 33, wherein to determine the colorimetric properties of the individual's skin comprises to measure spectral absorption and filtering out melanin contribution to the spectral absorption.

50. The system of claim 49, wherein to measure the spectral absorption includes an analysis of ranges of wavelengths and an identification of shifts in the measured spectral absorption, the shifts in the measured spectral absorption being indicative that a medical status of the individual is worsening.

51. The system of claim 33, wherein the color space comprises is an XYZ color space.

52. The system of claim 33, wherein the color index includes a pallor index.

53. The system of claim 33, wherein the first vector and the second vector comprise radial vectors.

54. The system of claim 33, wherein the threshold is 10%.

55. The system of claim 33, wherein the threshold is 20%.

* * * * *